(12) United States Patent
Ladtkow et al.

(10) Patent No.: US 11,692,170 B2
(45) Date of Patent: Jul. 4, 2023

(54) SEPARATING COMPOSITE LIQUIDS

(71) Applicant: Terumo BCT, Inc., Lakewood, CO (US)

(72) Inventors: James R. Ladtkow, Broomfield, CO (US); Geoffrey M. Uhl, Littleton, CO (US); Jeremy P. Kolenbrander, Brighton, CO (US); Briden Ray Stanton, Highlands Ranch, CO (US)

(73) Assignee: Terumo BCT, Inc., Lakewood, CO (US)

( * ) Notice: Subject to any disclaimer, the term of this patent is extended or adjusted under 35 U.S.C. 154(b) by 370 days.

(21) Appl. No.: 16/915,818

(22) Filed: Jun. 29, 2020

(65) Prior Publication Data

US 2020/0325446 A1    Oct. 15, 2020

Related U.S. Application Data

(62) Division of application No. 15/700,303, filed on Sep. 11, 2017, now Pat. No. 10,704,023, which is a
(Continued)

(51) Int. Cl.
| | |
|---|---|
| *C12N 5/078* | (2010.01) |
| *A61M 1/26* | (2006.01) |
| *A61M 1/30* | (2006.01) |
| *A61M 1/02* | (2006.01) |
| *A61M 1/34* | (2006.01) |

(Continued)

(52) U.S. Cl.
CPC ......... *C12N 5/0641* (2013.01); *A61M 1/0209* (2013.01); *A61M 1/26* (2013.01); *A61M 1/262* (2014.02); *A61M 1/30* (2013.01); *A61M 1/303* (2014.02); *A61M 1/308* (2014.02); *A61M 1/3496* (2013.01); *A61M 1/3616* (2014.02); *A61M 1/3693* (2013.01);
(Continued)

(58) Field of Classification Search
None
See application file for complete search history.

(56) References Cited

U.S. PATENT DOCUMENTS

| | | |
|---|---|---|
| 3,064,647 A | 11/1960 | Earl |
| 4,086,924 A | 5/1978 | Latham, Jr. |
(Continued)

FOREIGN PATENT DOCUMENTS

| | | |
|---|---|---|
| JP | S53-53194 | 5/1978 |
| JP | H11-503966 A | 4/1999 |
(Continued)

OTHER PUBLICATIONS

International Search Report and Written Opinion, PCT/US2014/016861, dated Jun. 3, 2014.

*Primary Examiner* — David W Berke-Schlessel
(74) *Attorney, Agent, or Firm* — Harness, Dickey & Pierce, P.L.C.

(57) ABSTRACT

Described are embodiments that include methods and devices for separating composite liquids into components. Embodiments involve the use of a flexible membrane for separating a composite liquid into components. The composite liquid may include, in embodiments, a cellular containing liquid, such as whole blood or components of whole blood. In one specific embodiment, the composite liquid is a buffy coat.

11 Claims, 14 Drawing Sheets

Related U.S. Application Data division of application No. 14/182,534, filed on Feb. 18, 2014, now Pat. No. 9,758,764.

(60) Provisional application No. 61/766,072, filed on Feb. 18, 2013.

(51) Int. Cl.
*A61M 1/36* (2006.01)
*B04B 5/04* (2006.01)

(52) U.S. Cl.
CPC ......... *A61M 1/3696* (2014.02); *B04B 5/0442* (2013.01); *B04B 2005/0471* (2013.01)

(56) References Cited

U.S. PATENT DOCUMENTS

| | | | |
|---|---|---|---|
| 4,421,503 A | 12/1983 | Latham, Jr. et al. | |
| 5,674,173 A | 10/1997 | Hlavinka et al. | |
| 5,722,926 A | 3/1998 | Hlavinka et al. | |
| 5,885,239 A | 5/1999 | Headley et al. | |
| 5,906,570 A | 5/1999 | Langley et al. | |
| 5,913,768 A | 6/1999 | Langley et al. | |
| 5,939,319 A | 8/1999 | Hlavinka et al. | |
| 5,951,877 A | 9/1999 | Langley et al. | |
| 6,071,422 A | 6/2000 | Hlavinka et al. | |
| 6,354,986 B1 | 3/2002 | Hlavinka et al. | |
| 7,201,848 B2 | 4/2007 | Antwiler et al. | |
| 7,857,744 B2 | 12/2010 | Langley et al. | |
| 7,963,901 B2 | 6/2011 | Langley et al. | |
| 8,057,377 B2 | 11/2011 | Holmes et al. | |
| 8,173,027 B2 | 5/2012 | Berg et al. | |
| 8,900,112 B2 * | 12/2014 | Holmes | B04B 5/0428 494/45 |
| 8,992,402 B2 | 3/2015 | Holmes | |
| 9,758,764 B2 | 9/2017 | Ladtkow et al. | |
| 2007/0203444 A1 | 8/2007 | Felt et al. | |
| 2007/0209708 A1 | 9/2007 | Hermann et al. | |
| 2008/0147240 A1 * | 6/2008 | Hudock | B04B 5/0428 700/266 |
| 2011/0136646 A1 * | 6/2011 | Pearce | A61M 1/3693 494/5 |
| 2011/0152055 A1 | 6/2011 | Pittinger et al. | |
| 2012/0129674 A1 | 5/2012 | Nash et al. | |
| 2012/0316051 A1 | 12/2012 | Holmes | |
| 2017/0369844 A1 | 12/2017 | Ladtkow et al. | |

FOREIGN PATENT DOCUMENTS

| | | |
|---|---|---|
| JP | H11-511686 A | 10/1999 |
| WO | 89/02273 A1 | 3/1989 |
| WO | 96/11747 A2 | 4/1996 |
| WO | 96/33023 A1 | 10/1996 |

\* cited by examiner

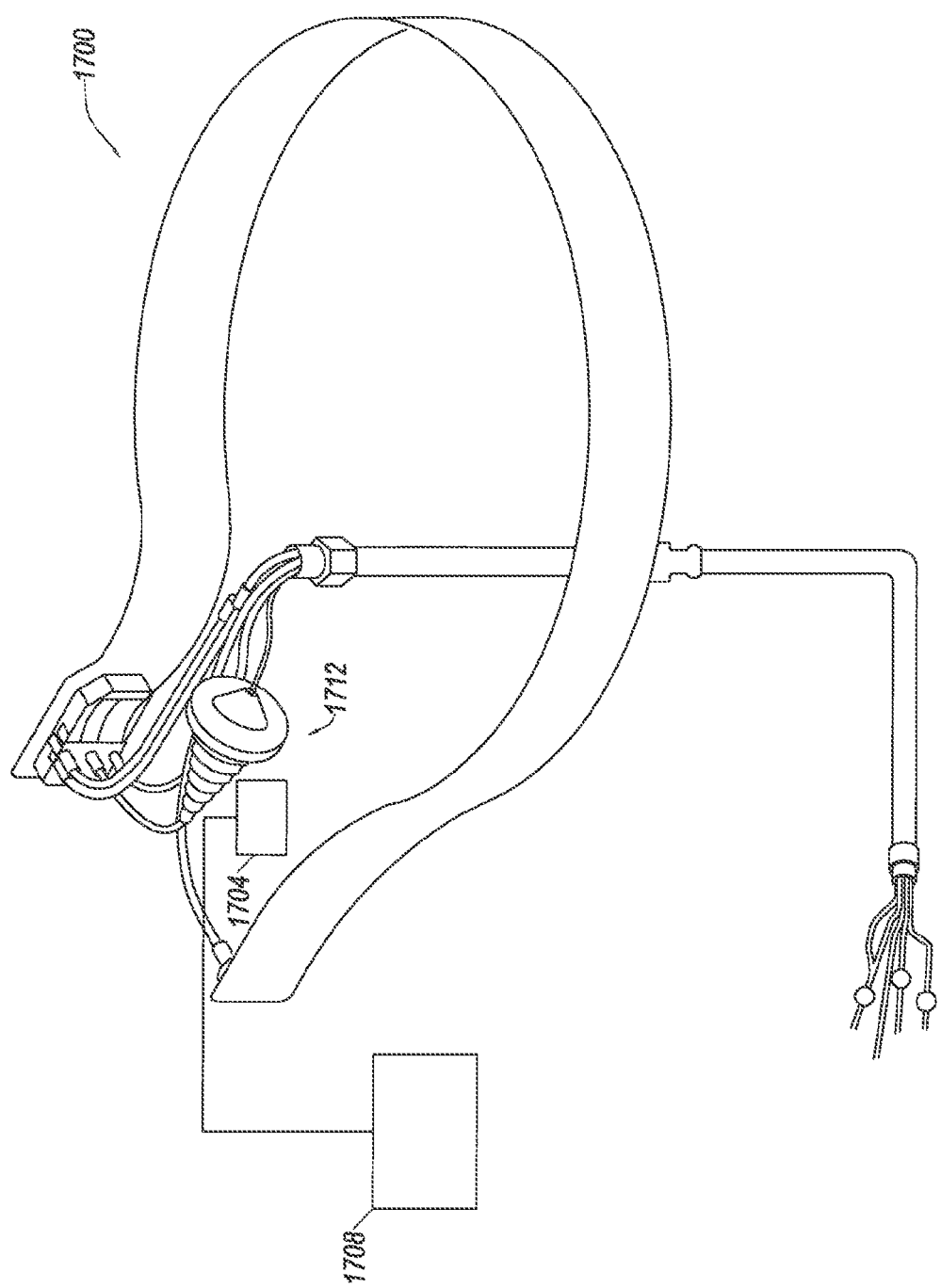

SEPARATING COMPOSITE LIQUIDS

CROSS-REFERENCE TO RELATED PATENT APPLICATION(S)

This patent application is a divisional, and claims priority to, U.S. patent application Ser. No. 15/700,303, entitled SEPARATING COMPOSITE LIQUIDS, filed on Sep. 11, 2017, which is a divisional, and claims priority to, U.S. patent application Ser. No. 14/182,534, entitled SEPARATING COMPOSITE LIQUIDS, filed on Feb. 18, 2014, and issued as U.S. Pat. No. 9,758,764, on Sep. 12, 2017. U.S. patent application Ser. No. 14/182,534 claims priority to U.S. Provisional Patent Application Ser. No. 61/766,072, entitled SEPARATING COMPOSITE LIQUIDS, filed on Feb. 18, 2013. Each of these applications is hereby incorporated by reference in its entirety as if set forth herein in full.

BACKGROUND

Apheresis blood processing plays an important role in a large number of therapeutic procedures. In these procedures, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation.

Both conventional blood collection and apheresis systems typically employ differential centrifugation methods for separating blood into its various blood components. In differential centrifugation, blood is circulated through a sterile blood processing vessel which is rotated at high rotational speeds about a central rotation axis. Rotation of the blood processing vessel creates a centrifugal force directed along rotating axes of separation, oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. A number of complementary separation techniques based on filtration, elutriation in a cell separation chamber and affinity-based techniques have been developed to achieve higher purities needed for use of blood components as therapeutic agents.

Embodiments of the present invention have been made in light of these and other considerations. However, the relatively specific problems discussed above do not limit the applicability of the embodiments of the present invention.

SUMMARY

The summary is provided to introduce aspects of some embodiments of the present invention in a simplified form, and is not intended to identify key or essential elements of the claimed invention, nor is it intended to limit the scope of the claims.

Embodiments of the present invention include methods and devices for separating composite liquids. Embodiments involve the use of a flexible membrane for separating a composite liquid into components. The composite liquid may be a cellular containing liquid, such as liquids containing whole blood or components of whole blood.

BRIEF DESCRIPTION OF THE DRAWINGS

Non-limiting and non-exhaustive embodiments are described with reference to the following figures.

FIG. 17 illustrates a system for monitoring a separation chamber.

DETAILED DESCRIPTION

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Embodiments below are described with respect to separating whole blood and blood components. However, this is done simply for illustrative purposes. It is noted that the embodiments are not limited to the description below. The embodiments are intended for use in products, processes, devices, and systems for separating any composite liquid. Accordingly, the present invention is not limited to separation of whole blood or blood components.

Figure 1:
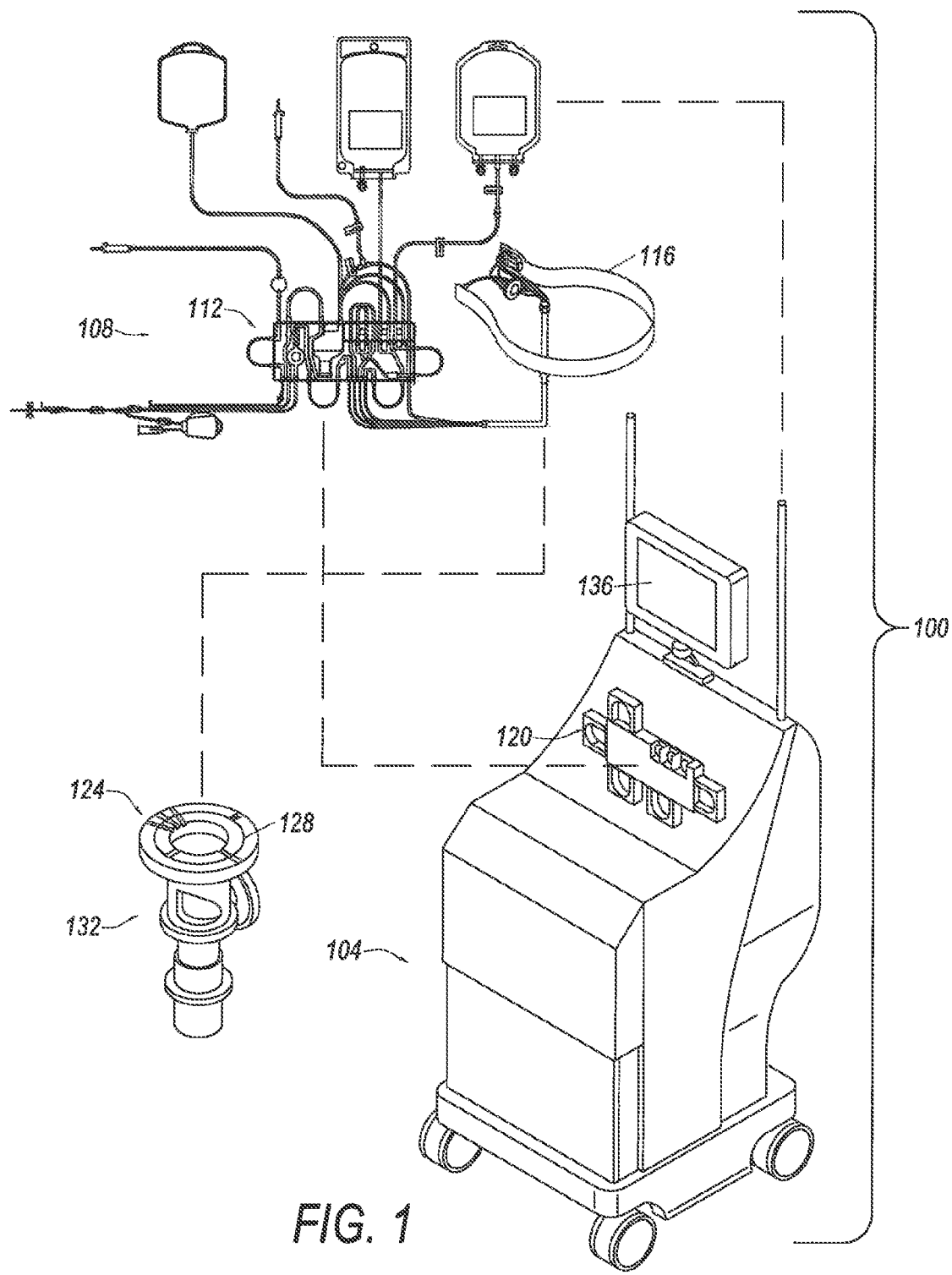
FIG. 1 illustrates one embodiment of an apheresis system, which can be used in, or with, embodiments.

FIG. 1 illustrates one embodiment of an apheresis system 100, which can be used in, or with, embodiments. In embodiments, apheresis system 100 provides for a continuous whole blood separation process. In one embodiment, whole blood is withdrawn from a donor and is substantially continuously provided to a blood component separation device 104 where the blood is separated into various components and at least one of these blood components is collected from the device 104. One or more of the separated blood components may be either collected for subsequent use or returned to the donor. In embodiments, blood is withdrawn from the donor and directed through a bag and tubing set 108, which includes an extracorporeal tubing circuit 112, and a blood processing vessel 116, which together define a closed, sterile and disposable system. The set 108 is adapted to be mounted in the blood component separation device 104. The separation device 104 includes a pump/valve/sensor assembly 120, which interfaces with the extracorporeal tubing circuit 112, and a centrifuge assembly 124, which interfaces with the blood processing vessel 116.

Examples of apheresis and other separation systems that may be used with embodiments of the present invention, e.g., as system 100, include the SPECTRA OPTIA® apheresis system, COBE® spectra apheresis system, and the TRIMA ACCEL® automated blood collection system, all manufactured by Terumo BCT, of Lakewood, Colo.

The centrifuge assembly 124 may include a channel 128 in a rotatable rotor assembly 132, which provides the centrifugal forces required to separate blood into its various blood component types by centrifugation. The blood processing vessel 116 may then be fitted within the channel 128. Blood can flow substantially continuously from the donor, through the extracorporeal tubing circuit 112, and into the rotating blood processing vessel 116. Within the blood processing vessel 116, blood may be separated into various blood component types and at least one of these blood component types (e.g., white blood cells, platelets, plasma, or red blood cells) may be removed from the blood processing vessel 116. Blood components that are not being retained for collection or for therapeutic treatment (e.g., platelets and/or plasma) are also removed from the blood processing vessel 116 and returned to the donor via the extracorporeal tubing circuit 112. Various alternative apheresis systems (not shown) may also make use of embodiments of the present invention, including batch processing systems (non-continuous inflow of whole blood and/or non-continuous outflow of separated blood components) or smaller scale batch or continuous RBC/plasma separation systems, whether or not blood components may be returned to the donor.

Operation of the blood component separation device 104 may be controlled by one or more processors included therein, and may advantageously comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory); communication/networking devices (e.g., wired such as modems/network cards, or wireless such as Wi-Fi); input devices such keyboard(s), touch screen(s), camera(s), and/or microphone(s); and output device(s) such as display(s), and audio system(s) a. In order to assist the operator of the apheresis system 100 with various aspects of its operation, the embodiment of the blood component separation device 104 (shown in FIG. 1) includes a graphical user interface 136 with a display that includes an interactive touch screen.

Figure 2:
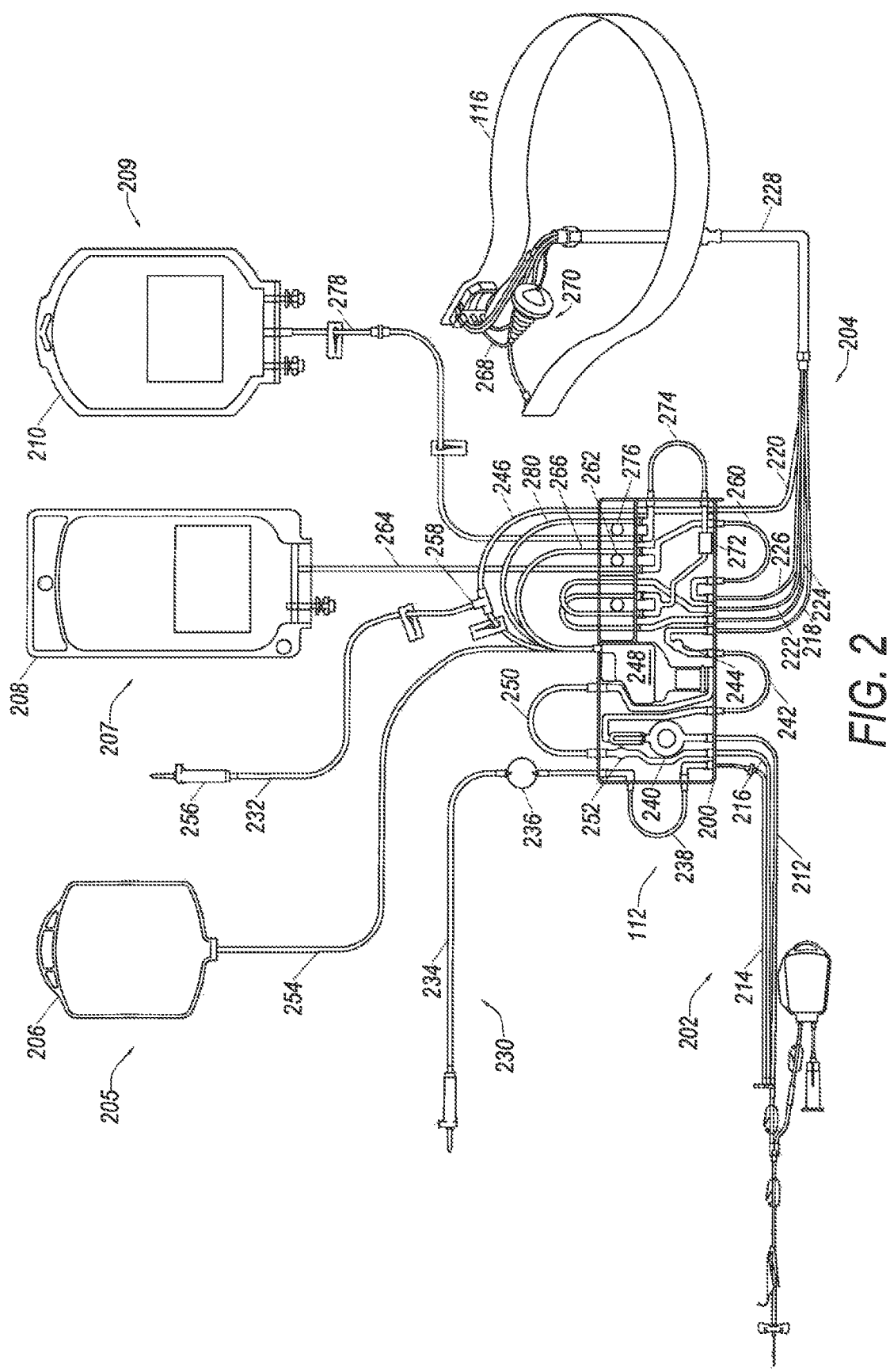
FIG. 2 illustrates a tubing and bag set for use in, or with, embodiments.

An embodiment of an extracorporeal tubing circuit is shown in FIG. 2, and as shown may include a cassette 200 and a number of tubing/collection assemblies 202, 204, 205, 207, and 209. A blood removal-return tubing assembly 202 provides a needle interface for withdrawing blood from a donor to the remainder of the tubing circuit 112 and for returning blood components and other fluids to the donor. A single needle configuration is shown, but other configuration such as a double needle interface may be used in other embodiments. Three lines 212, 214, 216 are provided in blood removal-return tubing assembly 202 for removal of blood from the donor. A cassette 200 is connected between the tubing assembly 202, which connects to the donor, and blood inlet/blood component tubing line sub-assembly 204, which provides the interface between cassette 200 and blood processing vessel 116. The cassette 200 orients tubing segments in predetermined spaced relationships within the cassette 200 for ultimate engagement with valve members on apheresis device 104. Such valves will, when activated, control flow through loops and tubing.

The tubing line sub-assembly 204 comprises five lines 218, 220, 222, 224, and 226, shown in FIG. 2, for transport of blood and components to and from the processing vessel 116. The five lines are encased in a sheath 228 that allows the one omega-two omega motion described in U.S. Pat. No. 4,425,112, hereby incorporated by reference as if set forth herein in full. An anticoagulant tubing assembly 230, a vent bag 206, a plasma collection bag 208, and a white blood cell collection bag 210 are also interconnected with cassette 200. Optionally, a red blood cell collection assembly might also be provided through an auxiliary line 232, as is known in the art. The extracorporeal tubing circuit 112 and blood processing vessel 116 are pre-connected to form a closed, sterilized, disposable assembly for a single use.

When the tubing circuit 112 has been mounted on the blood component separation device 104, saline solution (not shown) primes the tubing circuit through a line 234 and filter 236 (see FIG. 2). Saline flows through an internal passageway in the cassette 200 and through the line 214 to the distal end of the blood removal-return assembly 202. Saline can then flow up a blood withdrawal line 212 into the other tubes and passageways of the circuit 112 in preparation for blood processing. A supply or bag (not shown) of anticoagulant can then be connected to a distal end of the anticoagulant tubing assembly 230 in place of a saline supply. Anticoagulant solution flows past the filter 236 and a first pump loop 238 through the anticoagulant line 214 to the distal end of the blood removal assembly 202. The pump loop 238 and other pump loops described herein couple with peristaltic pumps on the blood processing device 104 in a known manner. The device 104 controls the direction and rate of flow of the fluids described herein by controlling the speed and direction of the peristaltic pumps and the position of various valves.

The blood removal line 212 conducts blood into the cassette 200, where the blood passes a first pressure sensor 240 and a second pump loop 242. A second pressure sensor 244, between second pump loop 242 with its associated pump and blood inflow line 218 to the blood processing vessel 116, senses the fluid pressure effective at an inlet to the blood processing vessel 116. Emanating from blood processing vessel 116 is an RBC outlet tubing line 220 of the blood inlet/blood component tubing assembly 204. The outlet tubing line 220 connects to an external loop 246 to a return reservoir 248. The return reservoir 248 contacts sensors on the device 104 that detect low and high fluid levels. The device 104 keeps the fluid in the reservoir 248 between these two levels by controlling flow out of the reservoir past a return pump loop 250 and a return pressure sensor 252. As the fluid level in the reservoir 248 is constantly rising and falling, a vent bag 206 connects to the reservoir 248 through a vent tube 254. Air can flow between the reservoir 248 and the vent bag 206 in a sterile manner. Fluid flows into a return tube 216 in the blood removal-return assembly 202. The blood removal-return assembly 202 also comprises the line 214 for priming or anti-coagulant as described above. If desired, red blood cells could be withdrawn through auxiliary line 232 and collected in a collection bag (not shown). Alternatively, a bag containing replacement fluid (not shown) is connected to a spike or Luer connector 256 on the replacement line 232, allowing replacement fluid to pass through the return loop 246 into the reservoir 248. Blood components and replacement fluid are then returned to the donor. In the present embodiment, replacement line 232 is connected to return loop 246 through a junction 258 and manual closures or clamps are provided to direct the flow of red blood cells and replacement fluid.

Plasma may also be collected from the blood processing vessel 116 into plasma collection assembly 208. When desired, plasma is withdrawn from the blood processing vessel 116 through plasma line 226 to a pump loop 260. A valve 262 diverts the plasma either into a collect tube 264 to the plasma bag 208, or into connecting loop or line 266 to the reservoir 248. Excess plasma in the reservoir 248 is returned to the donor in the same way as red blood cells, as described above.

White blood cells and platelets flow out of the blood processing vessel 116 through a cell line 268 into a cell separation chamber 270, embodiments of which are described below. The contents of the separation chamber 270 flow out of the separation chamber through an outlet. In the cassette 200, the fluid from the separation chamber 270 passes a red-green photo sensor 272, which may be used to control periodic flushing of white blood cells out of the cell separation chamber 270 into the collect bag 210. The selected cells flow through a pump loop or common line 274, which engages a peristaltic pump on the separation device 104. The pump loop 274 connects to a valved passageway in the cassette 200. The blood processing device 104 can control a valve 276 to direct white blood cells or other selected cells either into a collect tube 278 and thence into the collect bag 210, or into a connection loop or line 280 and thence into the reservoir 248. For platelet collection, excess white blood cells in the reservoir 248 may be returned to the donor in the same way as red blood cells and plasma, as described above. Alternatively, for mesenchymal stem cell (MNC) collection, wherein platelets are usually returned to the donor, the MNC are withdrawn into the collect tube 278 for storage in the collect bag 210.

During a blood removal, whole blood will be passed from a donor into tubing line 212 of blood removal tubing assembly 202. The blood is pumped by the device 104 via pump loop 242, to the blood processing vessel 116 via the cassette 200 and line 218 of the blood inlet/blood component tubing assembly 204. Separation processing then occurs on a substantially continuous basis in the blood processing vessel 116, i.e., blood flows substantially continuously therein, is continuously separated and flows as separated components there from. After separation processing in vessel 116, uncollected blood components are transferred from the processing vessel 116 to and through cassette 200 and into reservoir 248 of cassette 200, which is filled up to a predetermined level. The blood component separation device 104 may initiate a blood return sub mode wherein components may be returned to the donor through return line 216. The cycle between blood removal and blood return sub modes will continue until a predetermined amount of blood components have been harvested. In an alternative embodiment, a double needle scheme may be used so that blood may be removed from the donor and returned to a donor through two separate needles. See, for example, US Patent application 2010/160137, which illustrates a double needle disposable set and is hereby incorporated by reference as if set forth herein in full.

Figure 3:
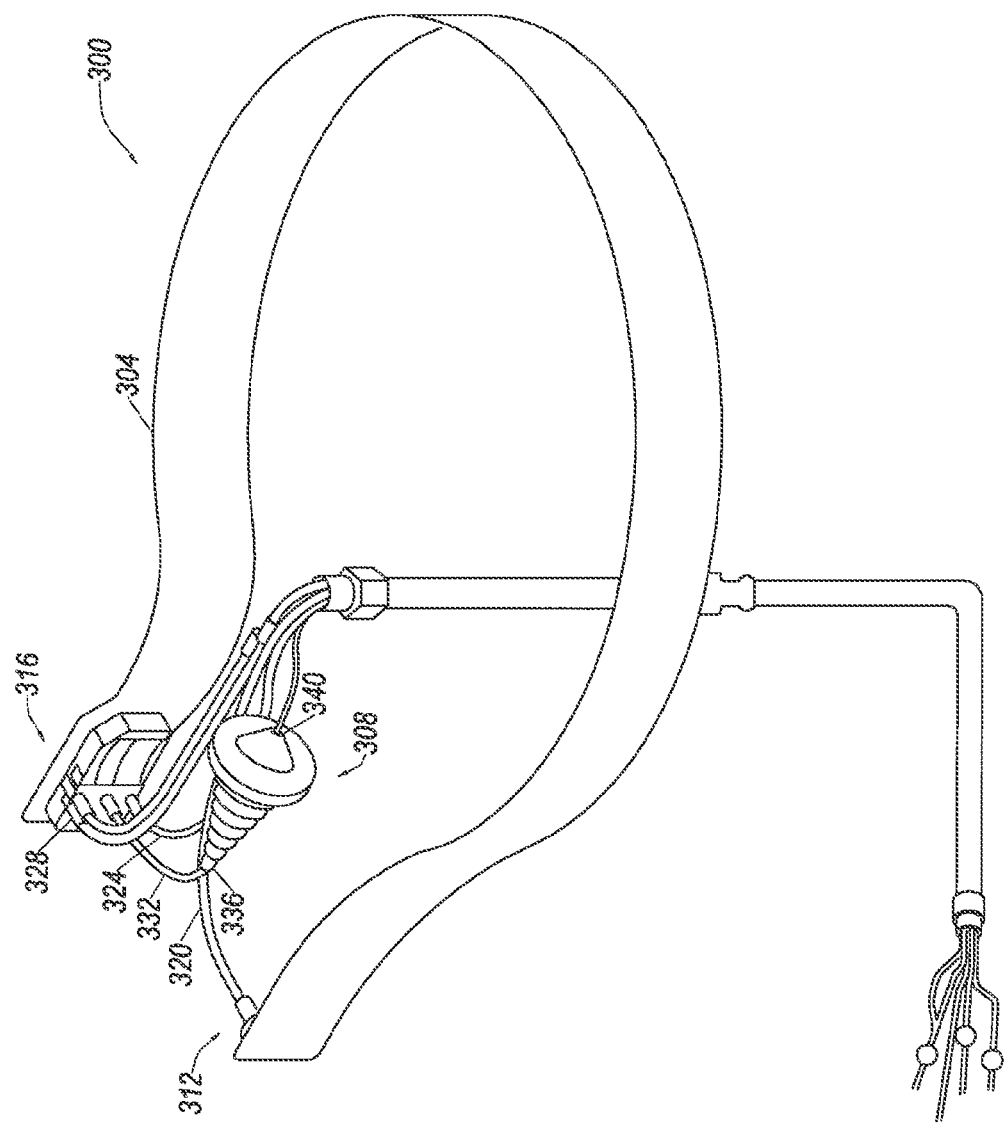
FIG. 3 illustrates a liquid processing vessel and a separation chamber according to an embodiment.

FIG. 3 illustrates a perspective view of an embodiment of a disposable set 300, which includes a liquid processing vessel 304 and a separation chamber 308. In one embodiment, disposable set 300 may be used to provide a blood processing disposable set, in which vessel 304 is used as vessel 116 and chamber 308 is used as chamber 270, described above (FIGS. 1 and 2). In other embodiments, however, disposable set 300 can be used to process composite liquids that do not include whole blood or blood components.

The liquid processing vessel 304 in embodiments has a generally annular flow path and includes an inlet portion 312 and an outlet portion 316. An inflow tube 320 connects to the inlet portion 312 for conveying a fluid into the blood processing vessel 304 for separating into components (e.g., whole blood into blood components). In one embodiment, set 300 is used in a centrifuge that rotates vessel 304, and as a result of centrifugal forces, separates liquids into components. In these embodiments, substances entering the inlet portion 312, flow around the vessel 304 and stratify according to differences in density in response to rotation of the centrifuge. The outlet portion 316 includes outlets for the components of the separated liquid.

In one example, when the composite liquid being separated includes whole blood, line 324 is used as a red blood cell (RBC) line, line 328 is used as a plasma line, and line 332 is used as the buffy coat or white blood cell line for removing the separated components from the processing vessel 304. In embodiments, each of the components separated in the vessel 304 is collected and removed in only one area of the vessel 304, namely the outlet portion 316.

In some embodiments a component separated in vessel 304 may be further processed to separate additional components. In these embodiments, the outlet of the line 332 is connected to the separation chamber inlet 336 to transfer intermediate density components to chamber 308.

In those embodiments, in which the liquid being separated includes whole blood the portion transferred into chamber 308 may be the buffy coat. Buffy coat including white blood cells or mesenchymal stem cells (MNC) may be transferred into separation chamber 308. Components initially separated in the processing vessel 304 are further separated in the cell separation chamber 308. For example, white blood cells could be separated from plasma and platelets in the buffy coat using the cell separation chamber 308. This further separation may take place, for example, by forming a saturated fluidized bed of particles in the cell separation chamber 308. Plasma and platelets may flow out of the cell separation chamber 308 through outlet 340. White blood cells or MNCs may be retained in the chamber 308. In other embodiments, other components may be separated such as granulocytes from a red blood cell component.

Figure 4:
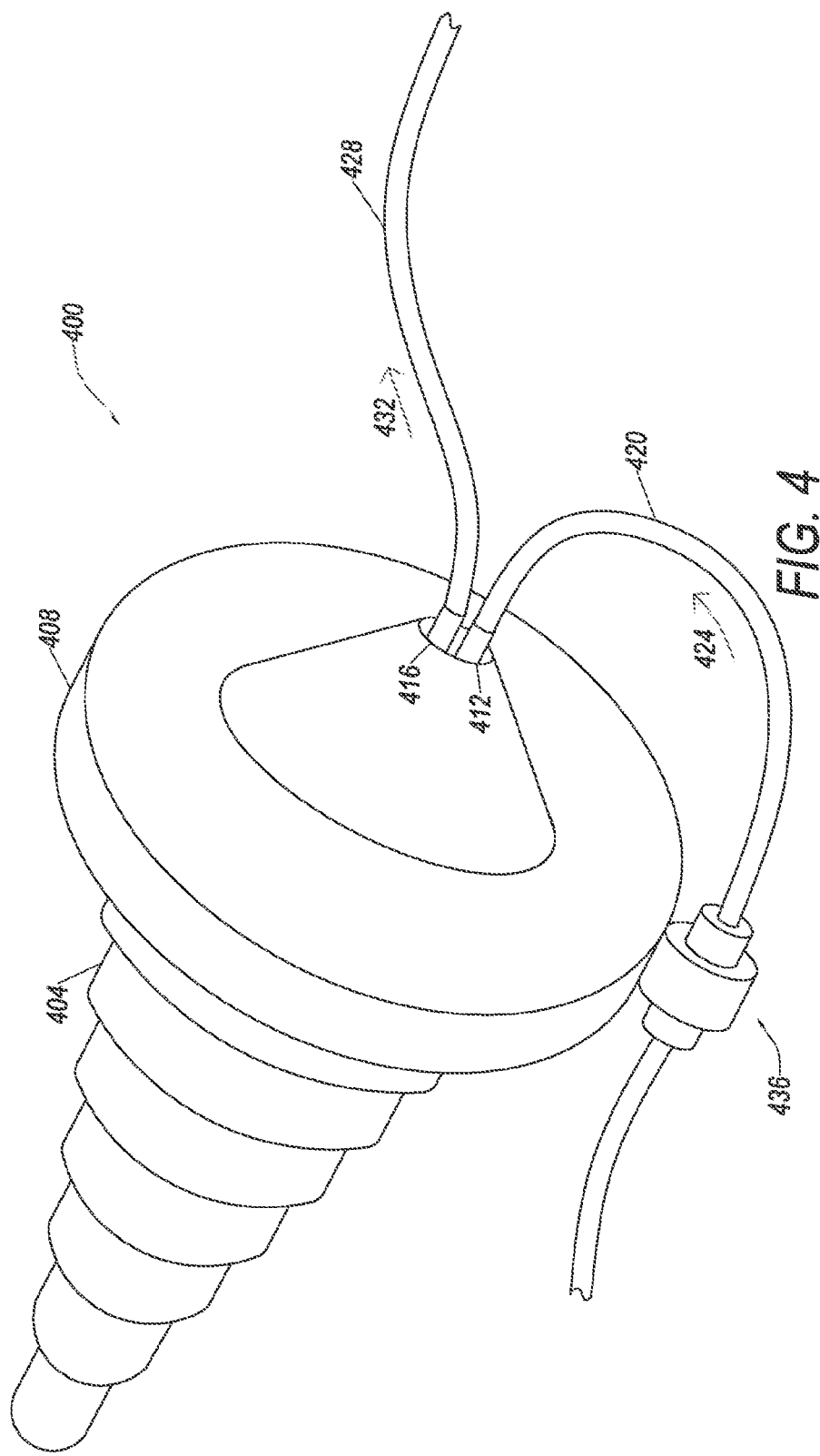
FIG. 4 illustrates a perspective view of a separation chamber according to an embodiment.

FIG. 4 illustrates a perspective view of an embodiment of a separation chamber 400. In embodiments, separation chamber 400 may be used as chamber 270 or 308 as described above. Chamber 400 includes a side wall 404 that defines a chamber volume (e.g., and interior volume), and a cap 408 that further defines the chamber volume. Chamber 400 may also include an inlet 412 and an outlet 416. In embodiments, fluid is transferred into chamber 400 using an input line 420, which is fluidly connected to inlet 412. After separation, components of the composite fluid are removed from chamber 400 through outlet 416, using an output line 428 fluidly connected to outlet 416. Arrow 424 illustrates the direction of flow of liquid into chamber 400 in some embodiments, while arrow 432 illustrates the direction of flow out of chamber 400 in some embodiments.

In some embodiments, a one-way valve 436 (e.g., a check valve), is fluidly connected to inlet 412 to prevent liquid from flowing in a direction opposite the direction indicated by arrow 424. In one embodiment, chamber 400 may be a cell separation chamber used to separate cells in a liquid buffy coat. The buffy coat may be processed in chamber 400, and one-way valve 436 may ensure that the buffy coat, or components separated from the buffy coat, do not flow in a direction opposite the direction indicated by arrow 424.

One-way valve 436 may be any one-way valve that allows flow of fluids in one direction but does not allow flow of the fluid in the opposite direction. Some non-limiting examples of one-way valves that may be used as one-way check valve 436 include ball check valves, diaphragm check valves, swing check valves, in-line check valves, lift check valves, stop check valves, duckbill check valves, and combinations thereof. These are merely some non-limiting examples, and other designs may be utilized as one-way valve 436.

It is noted that in embodiments, chamber 400 is subjected to centrifugal forces, such as may be created by blood component separation device 104 (FIG. 1). In these embodiments, one-way valve 436 may be designed to be able to operate properly under the centrifugal forces to which it will be subjected. As one example, the crack pressure, which is the minimum upstream pressure at which the valve 436 operates, may be designed to account for the centrifugal forces to which the valve 436 will be subjected.

Figure 5:
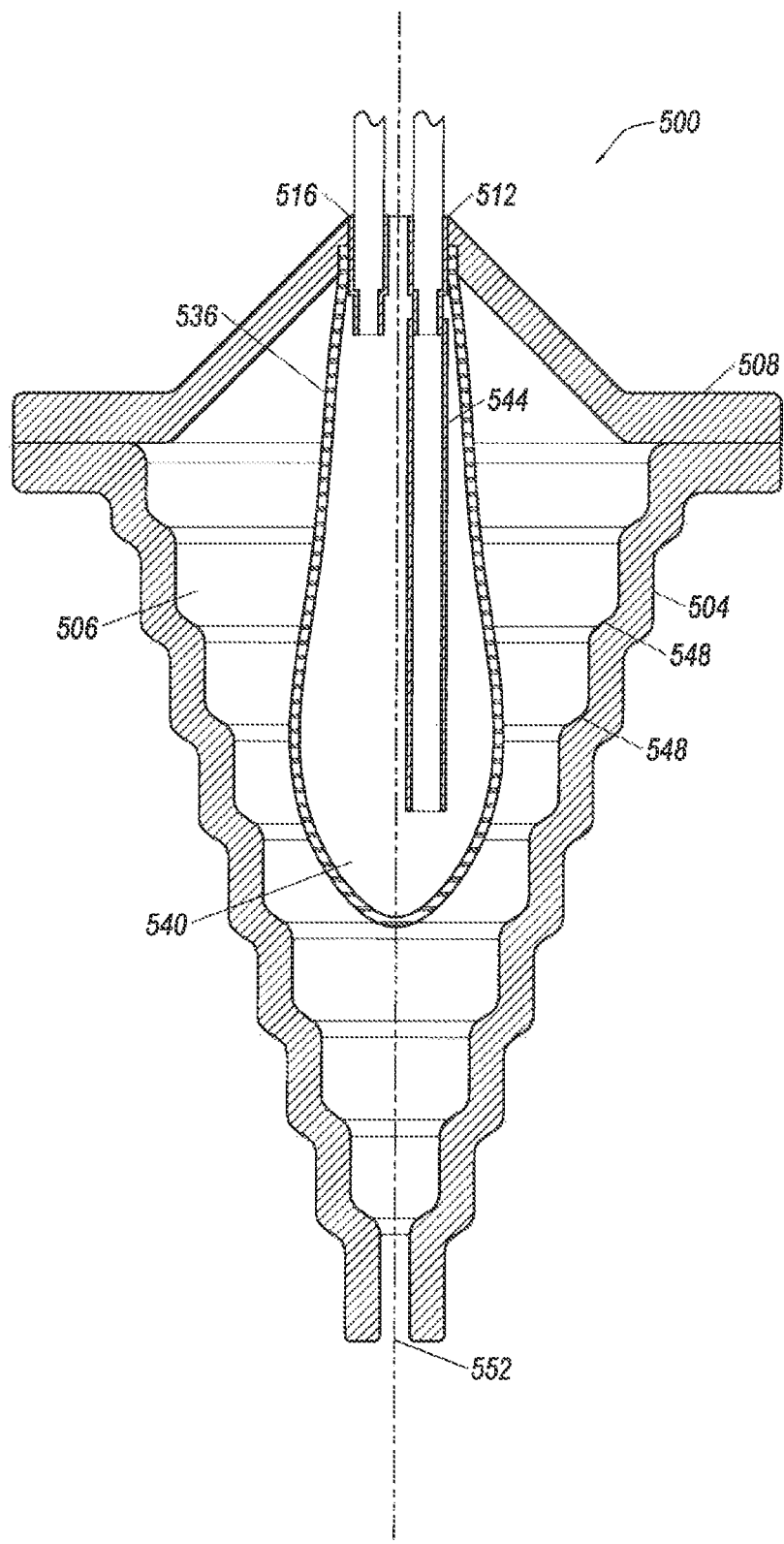
FIG. 5 illustrates a cross-sectional view of a separation chamber with a flexible membrane according to an embodiment.

FIG. 5 illustrates a cross section of a separation chamber 500 according to an embodiment. Chamber 500 includes side wall 504 that defines a chamber volume 506. In embodiments, chamber 500 includes a cap 508 that further defines volume 506. Chamber 500 further includes a flexible membrane 536 within chamber volume 506. The flexible membrane 536 defines a second volume, a membrane volume 540. An inlet 512 of chamber 500 is in fluid communication with the membrane volume 540 to allow composite liquids to enter membrane volume 540. In embodiments, an inlet tube 544 may be fluidly connected to the inlet 512 and extend within membrane volume 540 to direct the composite liquid into a particular portion of volume 540, e.g., a bottom portion of membrane volume 540. An outlet 516 is also in fluid communication with the membrane volume 540 to allow composite liquid and components to be transferred out of membrane volume 540. In addition, chamber 500 includes a vent 552 that allows a fluid, such as air to enter and escape chamber volume 506. The chamber 500 also comprises a plurality of steps 548 on an interior surface of side wall 504. As described in greater detail below, the plurality of steps 548 may be useful in separating a composite liquid into components.

Embodiments of chamber 500 may include various materials. In some embodiments, side wall 504 and cap 508 may be made of polymeric materials, some non-limiting examples including polyethylene terephthalate (PET) and copolymers thereof such as PETG. The side wall 504 and cap 508 may be formed by any appropriate forming process such as blow molding (e.g., extrusion blow molding, injection blow molding, stretch blow molding, etc.). Additionally, side wall 504 and cap 508 may be attached using any appropriate process including, without limitation, over-molding, solvent welding, adhesives, radio frequency welding, ultrasonic welding, etc.

Figure 6:
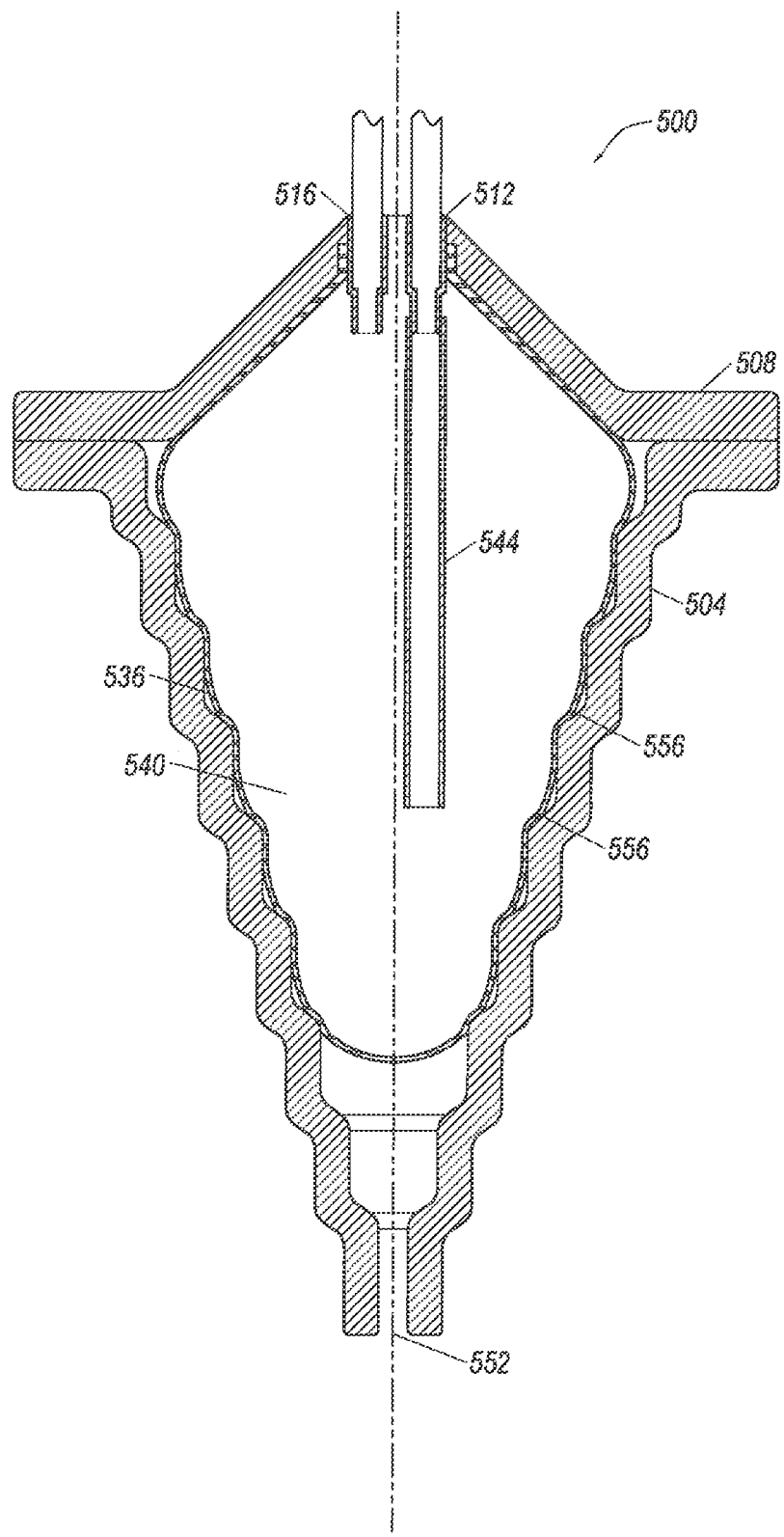
FIG. 6 illustrates a cross-sectional view of the separation chamber of FIG. 5 with the flexible membrane expanded.

Embodiments provide for flexible membrane 536 to expand when liquid is transferred into membrane volume 540 and a composite liquid is separated into components. FIG. 6 illustrates an embodiment of chamber 500 with flexible membrane 536 in an expanded state, which results in membrane volume 540 also expanding. It is noted that in operation, a composite liquid would be in membrane volume 540, however in order to simplify FIG. 6, the composite liquid is not shown.

Flexible membrane 536 may be maintained within volume 506 using a variety of different techniques. As one example, membrane 536 may be attached to cap 508. The membrane 536 may be attached, mechanically, by extending through a hole in cap 508 and attached to a top surface of cap 508 by mechanical fastening. In lieu of, or in addition to, mechanical fastening, the membrane 536 may be attached using other techniques such as over-molding, solvent welding, adhesives, radio frequency welding, ultrasonic welding, or other techniques.

In embodiments, the expansion of flexible membrane 536 occurs because of pressure within membrane volume 540. The head pressure of the composite liquid, in embodiments, controls the expansion and contraction of flexible membrane 536. In embodiments, in which the separation of a composite liquid in membrane volume 540 is effected through a centrifugal field, the pressure inside membrane volume 540, which causes flexible membrane 536 and membrane volume 540 to expand, is created by a centrifugal force acting on the volume of liquid within membrane volume 540. Accordingly, as liquid is transferred into membrane volume 540 and chamber 500 is subjected to a centrifugal field, flexible membrane 536 will begin to expand from its original shape (FIG. 5) as a result of the increase of pressure in membrane volume 540. The speed of the rotor in a centrifuge, which controls the force to which the liquid is subjected, can be used to control the expansion and contraction of the flexible membrane 536.

It is noted that in embodiments, flexible membrane 536 is made of materials that expand when subjected to pressure and have high viscoelasticities, such as elastomers. Some examples of materials that may be used to make flexible membrane 536, include without limitation, silicones, urethanes, latex, acrylics, copolymers, and other combinations thereof. The flexible membrane may be manufactured using any suitable technique including, without limitation, blow molding, injection molding (e.g., liquid injection molding), casting, compression molding, extruding, and/or forming.

Also, because flexible membrane 536 comes in contact with the composite liquid, it may be made of materials that are compatible with the composite liquid that will be separated in membrane volume 540. As one example, when chamber 500 is used to separate components of a buffy coat (see description of FIGS. 1-3) above, because the components of the buffy coat once separated may be introduced into a patient, the materials used in these embodiments of flexible membrane 536 may be biocompatible with the buffy coat and the components of the buffy coat. As one example, a flexible membrane used in separating buffy coat may be made from silicone.

In embodiments, membrane 536 is designed so that under the conditions of separation (e.g., volume of liquid in membrane volume 540, centrifugal force to which membrane 536 is subjected, and materials properties of membrane 536) an outside surface of the flexible membrane 536 contacts an inside surface of side wall 504, as shown in FIG. 6. When in contact with the inside surface of side wall 504, the flexible membrane 536 is flexible and takes on the shape of the inside surface of the side wall 504. For example, as shown in FIG. 6, flexible membrane 536, when in contact with side wall 504, has a plurality of steps 556 on its inside surface, that correspond to the plurality of steps 548 on the inside surface of side wall 504.

The ability of membrane 536 to reflect the contours of the inside surface of side wall 504 may be useful in some embodiments, because the side wall 504 may be designed to assist in separation of components in a composite liquid. As one example, when side wall 504 is used to separate white blood cells (or in some embodiments mesenchymal stem cells and/or mononuclear cells, etc.) from platelets in a buffy coat, the plurality of steps 548 on side wall 504 assists in creating a saturated platelet bed which traps white blood cells (or in some embodiments mesenchymal stem cells) at the lower section of chamber 500. The buffy coat flow rate into chamber 500 may be controlled to lift the platelets out of the centrifugal field to which chamber 500 is being subjected while white blood cells are trapped in the lower section. Accordingly, the flexible membrane 536 is designed to maintain the step design by having the corresponding steps 556 on its interior surface when in contact with the interior surface of side wall 504, e.g., during separation of a buffy coat. Some examples of designs used on the inside surface of a chamber for collecting components, such as cells, are described in U.S. Pat. Nos. 5,674,173, 5,939,319, 5,722,926, 5,913,768, 5,951,877, 5,906,570, and 6,071,422, which are hereby incorporated by reference in their entirety as if set forth herein in full.

In embodiments, flexible membrane 536 is designed to contract, e.g., return to its original shape (see FIG. 5), after pressure within membrane volume 540 is reduced, e.g., by reducing the speed of a rotor of a centrifuge, which reduces the centrifugal force on the liquid in the membrane volume. This contraction assists in removing components of a composite liquid that have been separated. Adding to the example noted above, when chamber 500 is used to separate white blood cells (or in some embodiments mesenchymal stem cells) from platelets in a buffy coat, the white blood cells may be trapped at a lower section of chamber 500. During separation, pressure within membrane volume 540 increases and flexible membrane 536 expands and contacts the inside surface of sidewall 504. Buffy coat is continuously transferred into the membrane volume 540 where the white blood cells are separated from the platelets and are trapped at the bottom of membrane volume 540. After the separation process, pressure within membrane volume 540 is reduced, e.g., by reducing the centrifugal force and/or the volume of buffy coat transferred into membrane volume 540. In these embodiments, the flexible membrane 536 is designed so that its elastic properties will shrink the membrane 536, as well as volume 540, back towards its original shape, shown in FIG. 5. The contraction of membrane volume 540 will effectively squeeze the white blood cells out of membrane volume 540. In embodiments, reducing the pressure may be performed suddenly, e.g., sudden reduction in speed of a rotor creating the centrifugal forces, to further enhance the squeezing effect.

The ability to squeeze components from membrane 536 allows the components to be more efficiently collected. In embodiments, having flexible membrane 536, improves the recovery of components such as white blood cells or mesenchymal stem cells, compared to chambers that do not include the flexible membrane 536.

In embodiments chamber 500 may be part of a disposable set, such as set 108 (FIGS. 1 and 2) and be used as chamber 270. In other embodiments, only portions of chamber 500 are part of the disposable set and the other portions may be used, e.g., permanent or reposable. For example, in one embodiment, cap 508, membrane 536, and inlet tube 544 may be part of a disposable set, with side wall 504 being permanent or reposable.

The embodiments described in FIGS. 5 and 6 are for illustrative purposes only and the present invention is not limited to the specific design and features of FIGS. 5 and 6. For example, in some embodiments, side wall 504 may be a single molded piece that completely defines chamber volume 506. In these embodiments, side wall 504 completely defines the chamber volume 506 and would include a portion that is similar to cap 508, eliminating the need for a cap. Other variations may occur to persons of ordinary skill in the art. The description below describes examples of other variations of embodiments that are within the scope of the present invention.

Figure 7:
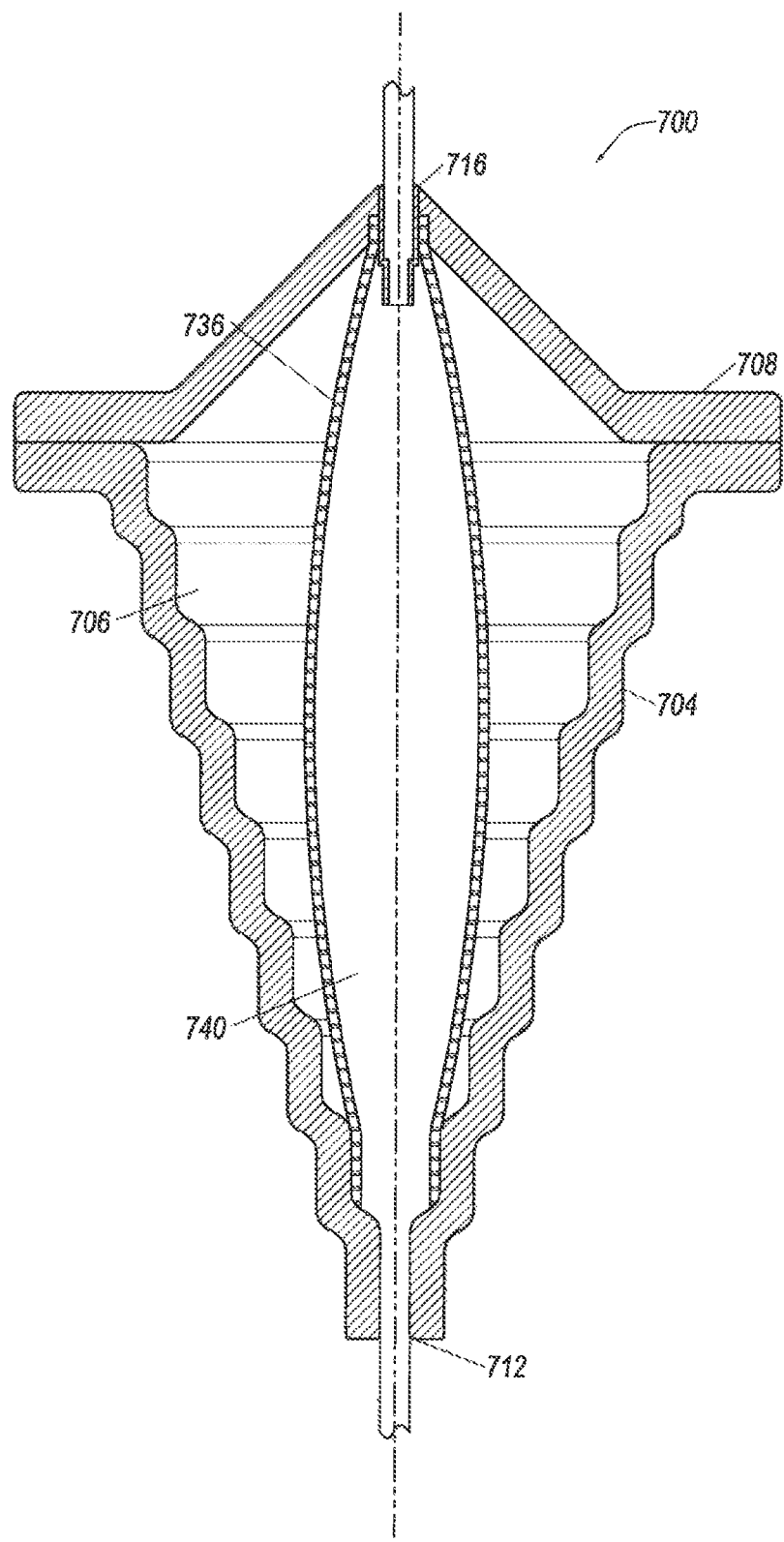
FIG. 7 illustrates a separation chamber with a flexible membrane according to a second embodiment.

FIG. 7 illustrates a cross section of a separation chamber 700 with a flexible membrane 736 according to another embodiment. Chamber 700 may include, in embodiments, all or some of the features described above with respect to chamber 500. Chamber 700 includes a side wall 704 that defines a chamber volume 706, a cap 708, an inlet 712, an outlet 716, and a flexible membrane 736 that define a membrane volume 740. Although chamber 700, in embodiments, may include features similar to chamber 500 it also has some different features. For example, inlet 712 is located at a bottom of side wall 704 instead of on cap 708. Composite liquid in this embodiment is therefore transferred into membrane volume 740 at the bottom of volume 740. Components are transferred out of membrane volume 740 through outlet 716 which is located on cap 708. In this embodiment, there is no need for an input tube, such as tube 544 in chamber 500.

The flexible membrane 736 may be similar to flexible membrane 536, and in embodiments may provide the same features as discussed above with respect to flexible membrane 536, e.g., squeeze components after separation out of volume 740. However, membrane 736 does include some different features. Flexible membrane 736 is attached to cap 708 and the bottom of side wall 704. The membrane 736 may be attached, mechanically, by extending through a hole in cap 708 and a hole in the bottom of side wall 704. The membrane 736 may then be attached to a top surface of cap 708 and an outside surface of side wall 704 by mechanical fastening. In lieu of, or in addition to, mechanical fastening, the membrane 736 may be attached on both ends using other techniques such as over-molding, solvent welding, adhesives, radio frequency welding, ultrasonic welding, or other techniques.

Figure 8:
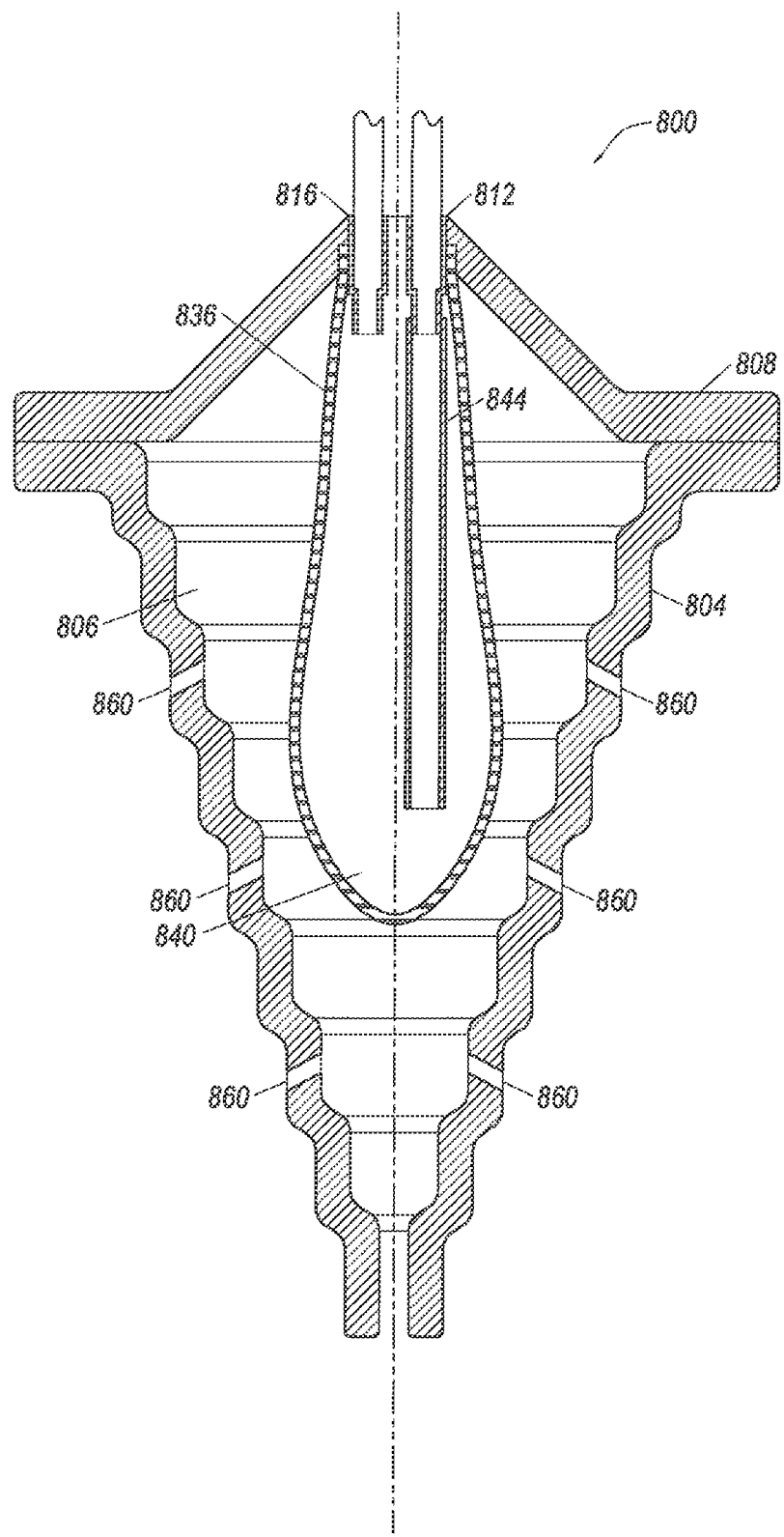
FIG. 8 illustrates a separation chamber with a flexible membrane according to a third embodiment.

FIG. 8 illustrates a cross section of a separation chamber 800 with a flexible membrane 836 according to yet another embodiment. Chamber 800 may include, in embodiments, all or some of the features described above with respect to chambers 500 and/or 700. Chamber 800 includes a side wall 804 that defines a chamber volume 806, a cap 808, an inlet 812, an outlet 816, an inlet tube 844, and a flexible membrane 836 that defines a membrane volume 840. Chamber 800, in embodiments, includes features similar to chambers 500 and/or 700. As one example, flexible membrane 836 may be similar to flexible membrane 536, and in embodiments may provide the same features as discussed above with respect to flexible membrane 536, e.g., squeeze components, after separation, out of volume 840.

Chamber 800 also has some additional features. For example, chamber 800 also has a plurality of vents 860. As will be appreciated, when membrane 836 expands it displaces fluid, namely air, from within chamber volume 806. If chamber 800 did not include vents, membrane 836 would have to compress the fluid within chamber volume 806 as it expanded. Having the plurality of vents 860, allows fluid to enter and escape chamber volume 806 as membrane 836 expands and contracts. Additionally, having more than one vent reduces the chance that a vent may get covered by membrane 836 when it expands, or blocked some other way, and not allow fluid to easily enter or escape volume 806. Having a plurality of vents allows alternative channels for fluid to escape and enter volume 806. This is different from chamber 500, which includes only one vent 552, which if covered would not allow fluid to enter or escape volume 506.

In other embodiments, one or more of the plurality of vents, may include a valve. The valve may control the rate at which fluid enters or escapes from the chamber volume 806. The valve may be designed to contribute in controlling the expansion and/or contraction of the membrane 836 expands and contracts. The valve may be any appropriate type of valve, including without limitation, ball valves, diaphragm valves, swing valves, lift valves, stop valves, and/or duckbill valves.

Figure 9:
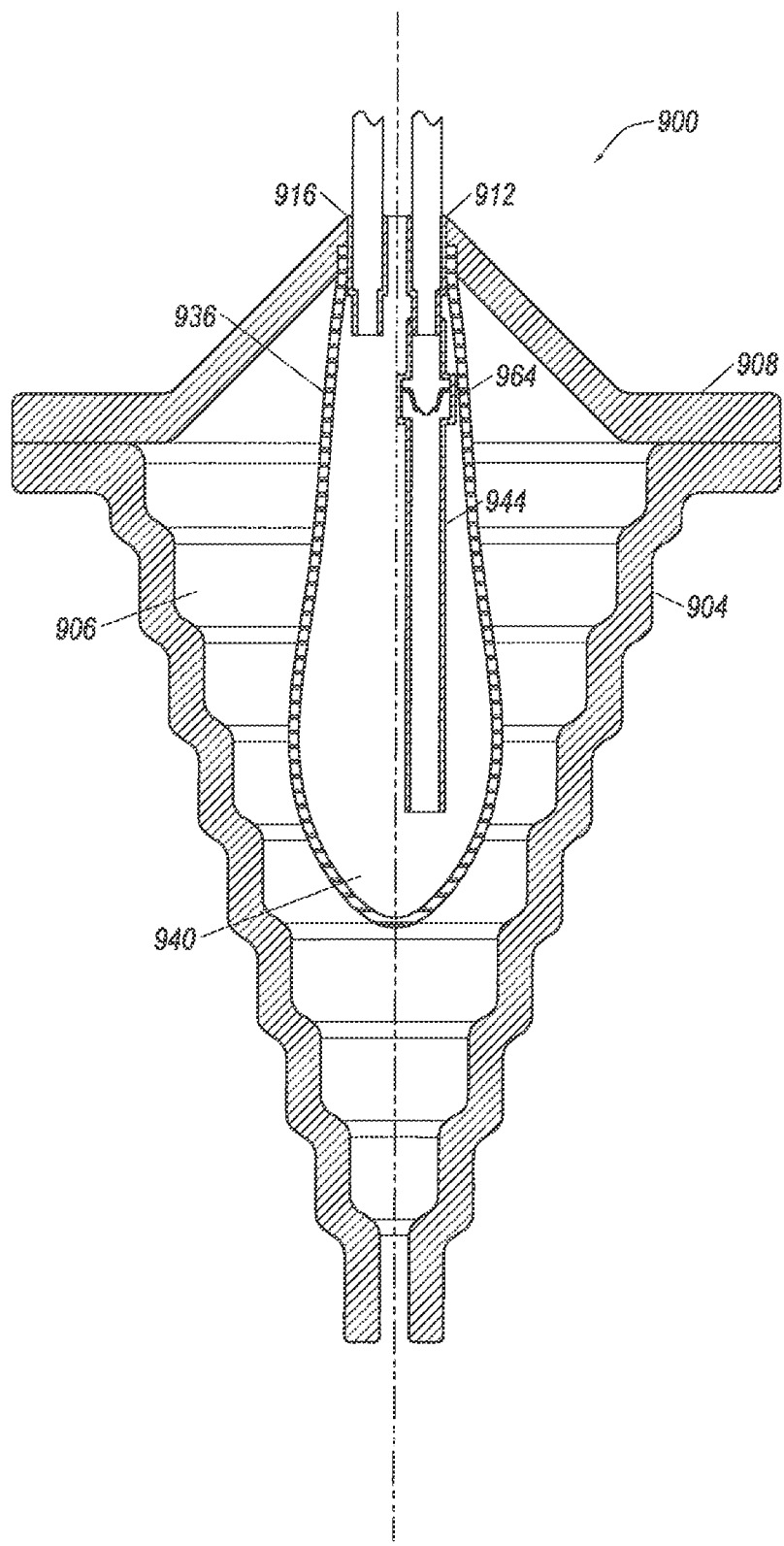
FIG. 9 illustrates a separation chamber with a flexible membrane according to a fourth embodiment.

FIG. 9 illustrates a cross section of a separation chamber 900 with a flexible membrane 936 according to another embodiment. Chamber 900 may include, in embodiments, all or some of the features described above with respect to chambers 500, 700, and/or 800. Chamber 900 includes a side wall 904 that defines a chamber volume 906, a cap 908, an inlet 912, an outlet 916, an inlet tube 944, and a flexible membrane 936 that defines a membrane volume 940. Chamber 900, in embodiments, includes features similar to chamber 500. As one example, flexible membrane 936 may be similar to flexible membrane 536, and in embodiments may provide the same features as discussed above with respect to flexible membrane 536, e.g., squeeze components, after separation, out of volume 940.

Chamber 900 also has some additional features. For example, chamber 900 has a one-way valve 964 that is within chamber volume 906, and more specifically within membrane volume 940. One-way valve 964 may be any one-way valve that allows flow of fluids in one direction but does not allow, or does not easily allow, flow of the fluid in the opposite direction. Some non-limiting examples of one-way valves that may be used as one-way valve 964 include ball check valves, diaphragm check valves, swing check valves, in-line check valves, lift check valves, stop check valves, duckbill check valves, and combinations thereof. These are merely some non-limiting examples, and other designs may be utilized as one-way valve 964. It is noted that in embodiments, chamber 900 is subjected to centrifugal forces, such as may be created by blood component separation device 104 (FIG. 1). In these embodiments, one-way valve 964 may be designed to be able to operate properly under the centrifugal forces to which it will be subjected. As one example, the crack pressure, which is the minimum upstream pressure at which the valve operates, may be designed to account for the centrifugal forces to which the valve will be subjected.

Figure 10:
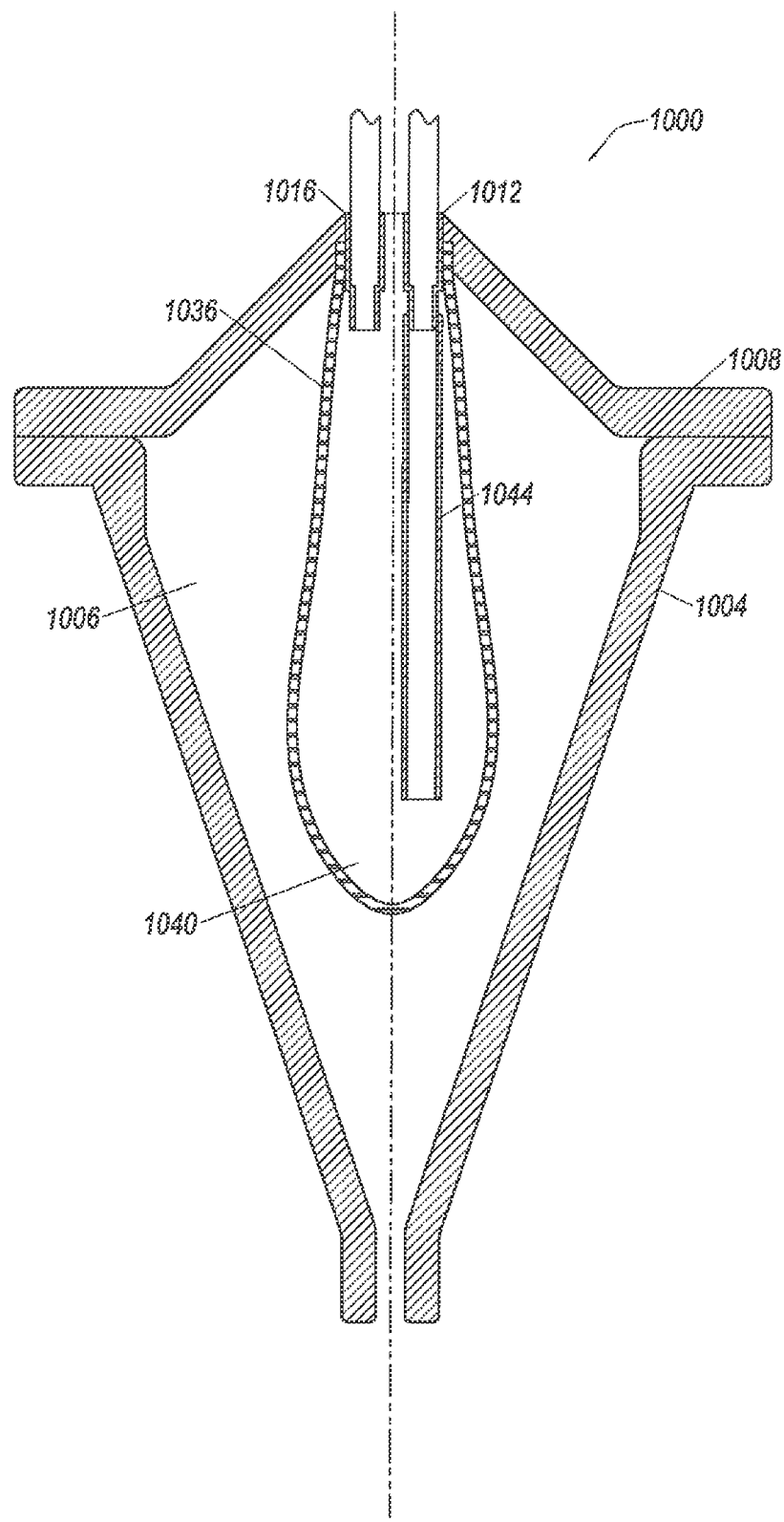
FIG. 10 illustrates a separation chamber with a flexible membrane according to a fifth embodiment.

FIG. 10 illustrates a cross section of a separation chamber 1000 with a flexible membrane 1036 according to another embodiment. Chamber 1000 may include, in embodiments, all or some of the features described above with respect to chambers 500, 700, 800, and/or 900. Chamber 1000 includes a side wall 1004 that defines a chamber volume 1006, a cap 1008, an inlet 1012, an outlet 1016, an inlet tube 1044, and a flexible membrane 1036 that defines a membrane volume 1040. Chamber 1000, in embodiments, includes features similar to chambers 500, 700, 800, and/or 900. As one example, flexible membrane 1036 may be similar to flexible membrane 536, and in embodiments may provide the same features as discussed above with respect to flexible membrane 536, e.g., squeeze components, after separation, out of volume 1040. However, chamber 1000 does include some different features. One example is that side wall 1004 does not include steps on its inside surface. Thus, when flexible membrane 1036 expands, the inside surface of flexible membrane 1036 will not have steps such as steps 556 (FIG. 5).

Figure 11:
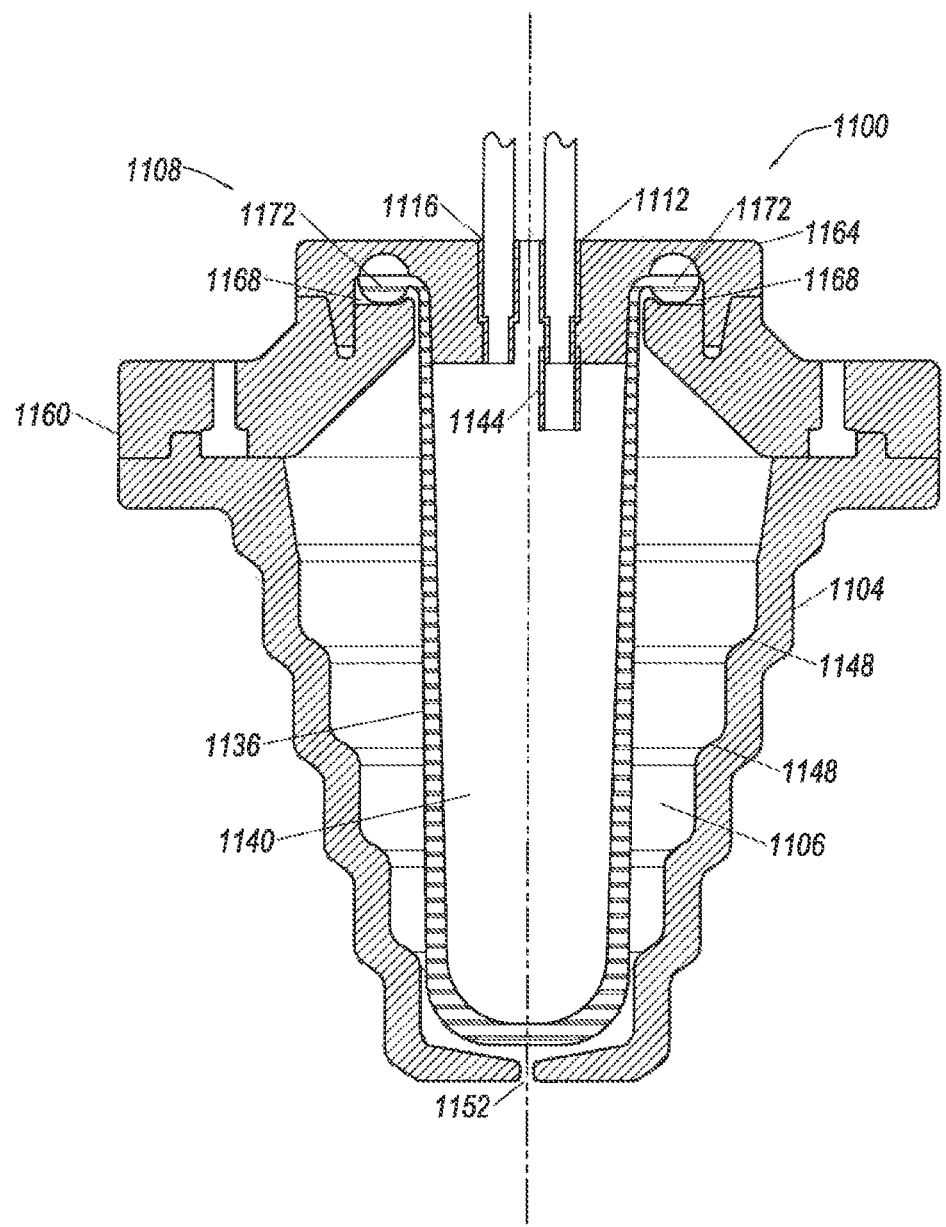
FIG. 11 illustrates a separation chamber with a flexible membrane according to a sixth embodiment.

FIG. 11 illustrates a cross section of a separation chamber 1100 with a flexible membrane 1136 according to another embodiment. Chamber 1100 may include, in embodiments, all or some of the features described above with respect to chambers 500, 700, 800, 900, and/or 1000. Chamber 1100 includes a side wall 1104 that defines a chamber volume 1106, a cap 1108, an inlet 1112, an outlet 1116, an inlet tube 1144, and the flexible membrane 1136 that defines a membrane volume 1140. Chamber 1100 also includes a vent 1152 that allows a fluid, such as air to enter and escape chamber volume 1106.

Similar to the membranes discussed above, membrane 1136 is designed to expand when a pressure within volume 1140 increases. The pressure in embodiments may increase as a result of liquid flowing into volume 1140. In other embodiments, chamber 1100 may be subjected to centrifugal force which may also increase the pressure within volume 1140. In yet other embodiments, a combination of liquid flowing into volume 1140 and a centrifugal force may cause the membrane 1136 to expand and increase the volume 1140. FIG. 11 illustrates membrane 1136 and volume 1140 in an initial state, without any liquid within volume 1140 or centrifugal force acting on chamber 1100 or membrane 1136.

Membrane 1136 is designed to expand and contact the inside surface of side wall 1104 when pressure within membrane volume 1140 is increased. In embodiments, when pressure within membrane volume 1140 reaches a particular level, membrane 1136 expands to contact the inside surface of side wall 1104. As a result of contacting the inside surface, membrane 1136 is designed to be flexible enough to reflect any contours that may be on the inside surface of side wall 1104. As noted above, embodiments of the side wall 1104 may be designed to assist in separation of components in a composite liquid.

In one embodiment, side wall 1104 is used to separate white blood cells (or in some embodiments mesenchymal stem cells) from platelets in a buffy coat, the plurality of steps 1148 on side wall 1104 assists in creating a saturated platelet bed which traps white blood cells (or in some embodiments mesenchymal stem cells) at the lower section of chamber 1100. The buffy coat flow rate into chamber 1100 may be controlled to lift the platelets out of the centrifugal field to which chamber 1100 is being subjected while white blood cells are trapped in the lower section. Accordingly, the flexible membrane 1136 is designed to maintain the step design by having corresponding steps on its interior surface when in contact with the interior surface of side wall 1104, e.g., during separation of a buffy coat. In these embodiments, flow of the buffy coat will be into volume 1140, which expands similar to membrane volume 540 shown in FIG. 6.

In embodiments, flexible membrane 1136 is not only designed to expand to contact the inside surface of side wall 1104 but also contract, e.g., return to its original shape, after pressure within membrane volume 1140 is reduced. This contraction assists in removing components of a composite liquid that have been separated, as described above. The squeezing of components from membrane 1140 allows the components to be more efficiently collected. In embodiments, having flexible membrane 1136, improves the recovery of components such as white blood cells or mesenchymal stem cells, compared to chambers that do not include the flexible membrane 1136.

In the embodiment shown in FIG. 11, membrane 1136 has a thickness that tapers along its length. As shown in FIG. 11 a top portion of membrane 1136 is thinner and a bottom portion of membrane 1136 is thicker. Membrane 1136 may be designed this way to accommodate greater pressures on the bottom portion than at the top portion. As noted above, chamber 1100 may be subjected to a centrifugal field, for example, by being mounted on a spinning rotor. The centrifugal field may be used to separate composite liquids into components. In embodiments, the top portion of membrane 1136 may be closer to an axis of rotation of the rotor, and consequently, experience less force than the bottom portion of membrane 1136, which may be further away from the axis of rotation. Therefore, the greater thickness of the bottom portion of membrane 1136 is provided to accommodate the larger forces experienced by this portion of the membrane 1136. The tapering thickness may allow membrane 1136 to expand and contract more uniformly when subjected to a centrifugal field, as the thicker bottom portion may require more force to expand, and in embodiments, will experience greater force from the centrifugal field.

As shown in FIG. 11, cap 1108 includes a first portion 1160 and a second portion 1164. The first portion 1160 and/or second portion 1164 may include a channel 1168. The channel 1168 is designed to accommodate a lip 1172 on membrane 1136. In embodiments, the lip 1172 may be an o-ring located at a top of membrane 1136.

In embodiments, the first portion 1160 of cap 1108 may be attached to a top of side wall 1104. The lip 1172 may then be positioned within channel 1168, which at the same time positions membrane 1136 within chamber volume 1106. The second portion 1164 of cap 1108 may then be attached to the first portion 1160. The combination of the first portion 1160, the second portion 1164, the channel 1168, and the lip 1172 provides a mechanism for securing membrane 1136 to cap 1108 and positioning it within chamber volume 1106. It is noted that the portions of cap 1108 may be attached using any suitable technique, some non-limiting examples including adhesives, welding (e.g., RF welding), solvent welding, and/or combinations thereof.

The description above of chambers 500, 700, 800, 900, 1000, and 1100 is provided for illustrative purposes and the present invention is not limited thereto. It is noted that the chambers 500, 700, 800, 900, 1000 and 1100 may be used in embodiments as cell separation chambers for separating a cellular component from a composite liquid, such as blood and blood components.

It is further noted that flexible membranes (e.g., 536, 736, 836, 936, 1036 and 1136) used in embodiments of the present invention, may have any shape. In embodiments, the shape may depend upon the shape of a side wall. For example, the side walls 504, 704, 804, 904, 1004, and 1104 have a conical shape (see FIGS. 5-11) however, in other embodiments, these side walls may have different shapes such as cylindrical, spherical, a prism, etc. In these other embodiments, it may be useful to have the flexible membranes also have different shapes. In yet other embodiments, the flexible membranes may have different shapes, even if the side wall is conical. FIGS. 12-16 illustrate different shapes that some embodiments of the flexible membrane may have.

Figure 13:
FIG. 13 illustrates a flexible membrane according to a second embodiment.
Figure 12:
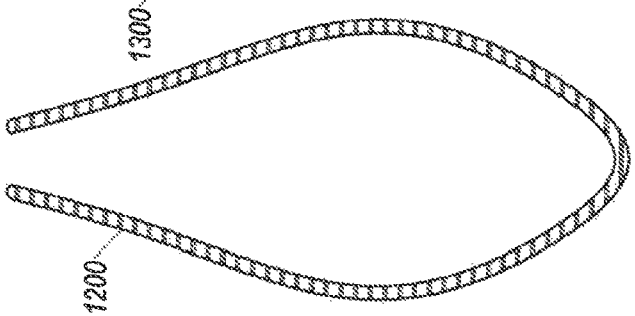
FIG. 12 illustrates a flexible membrane according to an embodiment.

FIG. 12 illustrates a cross section of a flexible membrane 1200 according to an embodiment. Flexible membrane 1200 is similar to flexible membranes 536, 736, 836, 936, 1036, and 1136 (see FIGS. 5-11). Flexible membrane 1200 has a tear drop shape. FIG. 13 illustrates a flexible membrane 1300 according to a different embodiment. As shown in FIG. 13, membrane 1300 has more of a cylindrical shape.

Figure 14:
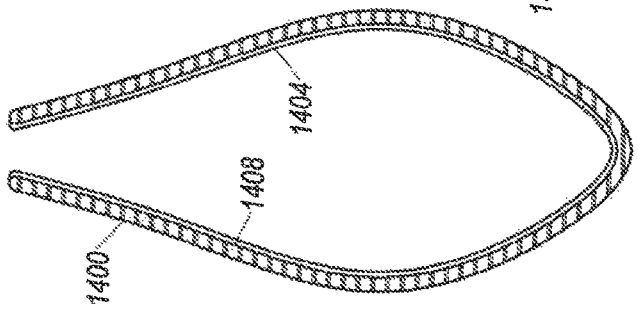
FIG. 14 illustrates a flexible membrane according to a third embodiment.

FIG. 14 illustrates a cross section of a flexible membrane 1400 according to another embodiment. Flexible membrane 1400 includes a coating 1404 on an interior surface 1408. In embodiments, the coating 1404 is used to impart additional properties to flexible membrane 1400. As one example, the coating 1404 may be used to protect the materials from which flexible membrane 1400 is made. This is useful in embodiments in which liquids that will contact membrane 1400 may be corrosive or otherwise incompatible with other materials of membrane 1400. In yet other embodiments, it may enhance separation by attracting components of a liquid to the interior surface 1408. For example, the coating 1404 may make the interior surface 1408 hydrophobic or hydrophilic depending on the liquid components being separated. In other embodiments, the coating 1404 may make flexible membrane 1400 more biocompatible. It is noted that coating 1404 does not have to be continuous, and may be a discontinuous layer on the inside surface of membrane 1400.

Figure 15:
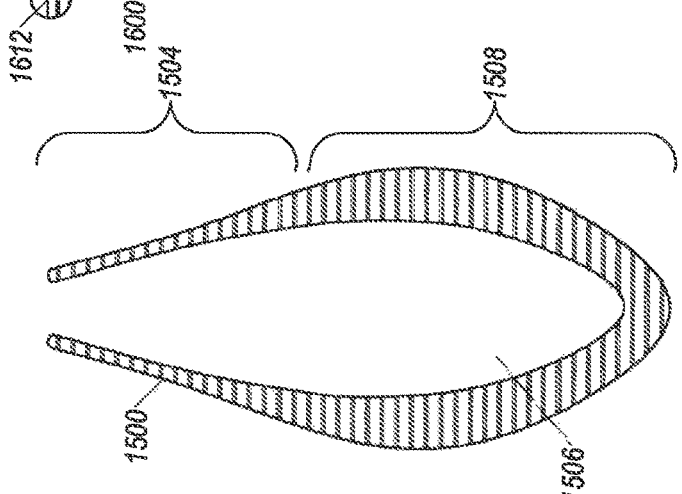
FIG. 15 illustrates a flexible membrane according to a fourth embodiment.

FIG. 15 illustrates a cross section of a flexible membrane 1500 according to another embodiment. Flexible membrane 1500 includes different thicknesses. A top portion 1504 is thinner than a bottom portion 1508. In embodiments, flexible membrane 1500 is subjected pressures that are not uniform. As one example flexible membrane 1500 is subjected to a centrifugal field, such as during a separation process that creates different pressures within membrane volume 1506. The difference in thicknesses of portions 1504 and 1508 will affect the expansion of flexible membrane 1500 in response to the pressures in volume 1506. Accordingly, the thickness of flexible membrane 1500 can be designed to control the expansion of membrane 1500. In one embodiment, flexible membrane 1500 may experience greater pressure on portion 1508 and less pressure on portion 1504. The different thicknesses shown in FIG. 15 may allow membrane 1500 to expand more uniformly despite the pressure variations.

It is noted that FIG. 15 is provided merely to illustrate that flexible membranes may have varying thicknesses in some embodiments. The variations in thickness may have a different design than that illustrated in FIG. 15, namely a tapered design. Other embodiments may include membranes that have portions of substantially uniform thickness and other portions of a different uniform thickness. Yet other embodiments may have some portions of uniform thickness and other portions of tapering thickness. Any design of a membrane with different thickness is contemplated to be within embodiments of the present invention. Moreover, in embodiments, any of the chambers (270, 500, 600, 700, 800, 900, 1000, and 1100) described above and shown in FIGS. 1-11 may utilize membranes with different thicknesses.

Figure 16:
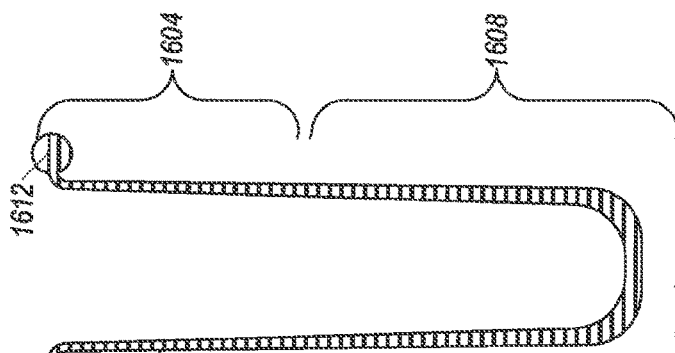
FIG. 16 illustrates a flexible membrane according to a fifth embodiment.

FIG. 16 illustrates a cross section of a flexible membrane 1600 according to another embodiment. Flexible membrane 1600 has a somewhat cylindrical shape and also includes portions with different thicknesses. As shown in FIG. 16, the thickness of membrane 1600 tapers from a thinner top portion 1604 to a thicker bottom portion 1608. Similar to membrane 1136 described above. As noted above, membrane 1136 may be subjected to a centrifugal field, for example, by being mounted on a spinning rotor. In embodiments, the top portion 1604 of membrane 1600 may be closer to an axis of rotation of the rotor, and consequently, experience less force than the bottom portion 1608 of membrane 1600, which may be further away from the axis of rotation. Therefore, the greater thickness of the bottom portion 1608 of membrane 1600 is provided to accommodate the larger forces experienced by this portion of the membrane. The tapering thickness may allow membrane 1600 to expand and contract more uniformly when subjected to a centrifugal field, as the thicker bottom 1608 portion may require more force to expand than the thinner top portion 1604.

In addition, membrane 1600 also includes a lip 1612, which in embodiments may be an o-ring. The lip may be used in embodiments to securely position the membrane within a chamber volume. In one embodiment, a first portion of a cap (of the chamber) includes a channel, into which the lip 1612 is positioned. A second portion of the cap can then be placed on top of the first portion to secure lip 1612 within the channel and secure membrane 1600 within a chamber volume (see e.g. FIG. 11).

FIGS. 12-16 are provided merely as examples, and flexible membranes according to embodiments may have other shapes including conical or more complicated shapes that have contours, curves, steps, ridges, channels, angles, or other shapes on an inside surface and/or an outside surface of the membrane Some embodiments may also include the use of membranes that have combinations of features illustrated in FIGS. 12-16 and/or combinations that include features illustrated and described above with other features not illustrated or described above.

FIG. 17 illustrates an embodiment of a system 1700 for monitoring a separation chamber, for example the expansion and contraction of a flexible membrane inside the separation chamber. System 1700 includes a sensor 1704 and a controller 1708. Sensor 1704 is in embodiments a sensor that can sense the expansion and contraction of a flexible membrane within chamber 1712. The sensor 1704 may be connected to controller 1708 which may control the pressure within the flexible membrane such as by increasing or decreasing the speed of a rotor of a centrifuge that is spinning chamber 1712, or, in some embodiments, controlling a pump that is transferring liquid into a membrane volume of the flexible membrane. In this way, system 1700 may control the expansion and contraction of the flexible membrane.

Sensor 1704 may be any suitable sensor including without limitation, optical sensors such as cameras, light sources (LED's, lasers), mirrors, fiber optics, photodetectors, and combinations thereof. The controller 1708 may be any combination of integrated circuits, microprocessor, memory, software, or other logic device(s) for processing signals from the sensor 1704.

The foregoing description is provided merely to illustrate that system 1700 may include sensors or other devices for monitoring the expansion and contraction of a flexible membrane. In embodiments, a system may include combinations of features described above with respect to FIG. 17 and/or combinations that include features that are not illustrated or described above.

Figure 18:
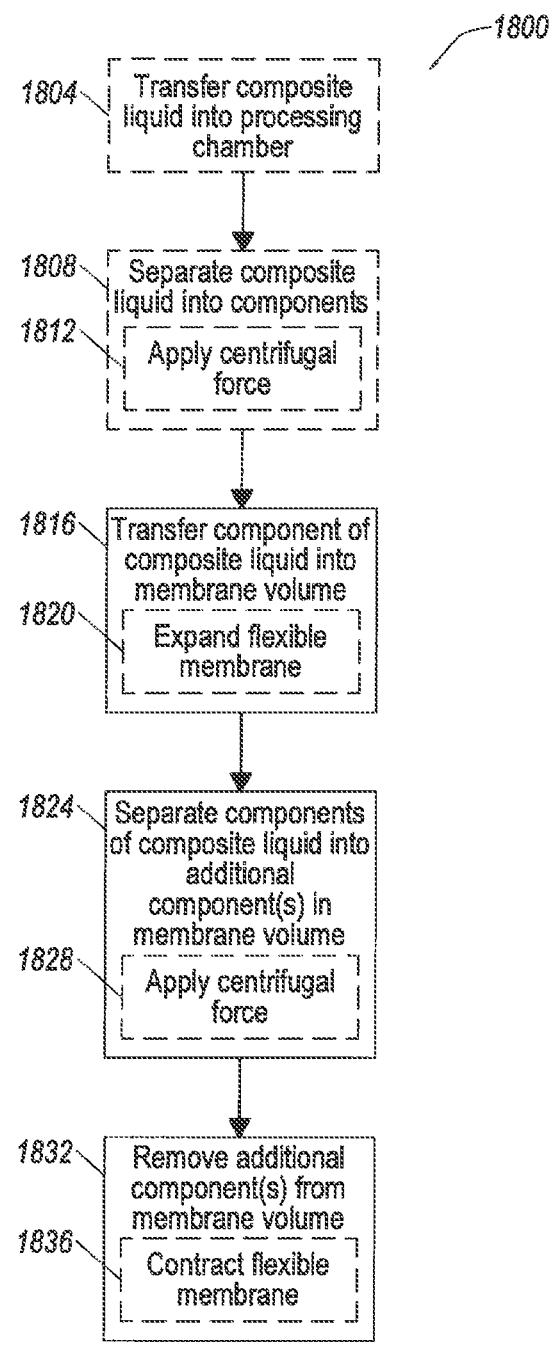
FIG. 18 illustrates a flow chart of a process for separating composite liquids such as whole blood containing liquids.

FIG. 18 illustrates flow chart 1800 which may be performed in embodiments of the present invention. Although specific components may be described below for performing steps in flow chart 1800, the present invention is not limited thereto. For example, some steps may be described as performed by a rotor in a centrifuge, while others are described as performed by a chamber or flexible membrane. This is done merely for illustrative purposes, because flow chart 1800 is not limited to being performed by any specific components, structures, or combinations thereof.

Flow 1800 begins at an optional step 1804 in which a composite liquid is transferred into a processing chamber. The composite liquid is in embodiments a whole blood containing liquid. Step 1804 may be performed using pumps and tubing such as tubing described above with respect to FIGS. 1 and 2. Additionally, the processing chamber may be part of a disposable set, such as described with respect to FIG. 2 above.

After step 1804, the composite liquid is separated at optional step 1808 into components. Step 1808 may in embodiments involve some sub-steps. For example, step 1808 may involve application of a centrifugal force at sub-step 1812. Sub-step 1812 may be performed in embodiments by a rotor and centrifuge that in some embodiments are part of an apheresis machine such as machine 100 (FIG. 1).

Following step 1808, at least one component separated from the composite liquid at step 1808 is transferred into a membrane volume at step 1816. It is noted that in some embodiments, step 1808 may involve transferring a composite liquid, which was not previously separated from a composite liquid. That is, the composite liquid transferred into a membrane at step 1816, in embodiments, may not have gone through any of steps 1804-1812.

Step 1816 may involve a number of sub-steps. In one embodiment, step 1816 involves sub-step 1820, where the flexible membrane is expanded. Sub-step 1820 may be performed in one embodiment by increasing a pressure within a membrane volume defined by the flexible membrane. In embodiments, the flexible membrane may be any one of the membranes (536, 736, 836, 936, 1036, 1136, 1200, 1300, 1400, 1500, or 1600) described above. Sub-step 1620 may involve increasing the pressure within the membrane volume by increasing the speed of a rotor in a centrifuge that in some embodiments is part of an apheresis machine. In other embodiments, in addition to, or instead of, changing the speed of the rotor of the centrifuge, more liquid may be introduced into the membrane volume.

After step 1816, the component transferred into the flexible membrane at step 1816 is separated at step 1824 into additional components. Step 1824 may in embodiments involve some sub-steps. For example, step 1824 may involve application of a centrifugal force at sub-step 1828. Sub-step 1828 may be performed in embodiments by a rotor and centrifuge that in some embodiments are part of an apheresis machine, e.g., machine 104 (FIG. 1).

After step 1824, the additional component(s) are removed from the flexible membrane at step 1832. Step 1832 may in embodiments involve some sub-steps. For example, step 1832 may involve contracting the flexible membrane at sub-step 1836. Sub-step 1836 in one embodiment may be performed by decreasing a pressure within a membrane volume defined by the flexible membrane. Sub-step 1836 may involve decreasing the pressure within the membrane volume by decreasing the speed of a rotor in a centrifuge that in some embodiments is part of an apheresis machine.

In embodiments, the present invention is directed to a cell separation chamber for separating components from liquids that include whole blood. In embodiments, it includes a rigid chamber that is lined with a membrane made of a flexible material such as latex or silicone. The rigid chamber is non-liquid contacting (e.g., non-blood contacting) and serves as a structural support for the membrane when it is inflated, e.g., expands and fills with liquid.

In some embodiments, the chamber is manufactured to have a flow through design where the membrane is anchored on both the top and bottom of the chamber. In this configuration the membrane may be similar to a cylinder. The membrane may include an inner and outer diameter each of which may be tapered, curved, or have a predetermined shaped. In other embodiments, the membrane may have a configuration where the membrane has a top down design, where the membrane may only be anchored/attached at the top of the chamber. In the top down design embodiment, the membrane may have a shape similar to a closed end cylinder with a round end. The walls may be tapered, curved, or shaped.

In some embodiments, the membrane and chamber may be part of a SPECTRA OPTIA® apheresis system, collection disposable set manufactured by Terumo BCT, of Lakewood, Colo. In embodiments, the membrane and chamber may be used for collecting mesenchymal stem cells (MNC's) or other types of cells. When a rotor of a centrifuge in an apheresis machine spins, the pressure of the fluid in the system may increase. Once the pressure exceeds a certain threshold level, the membrane may expand and inflate with liquid (e.g., a blood component) and may conform to the rigid walls of the chamber. At this higher pressure situation, the chamber may be filled with liquid, e.g., buffy coat and serves as a separation chamber which allows white blood cells (WBC's) to be entrained in the chamber while platelets flow through the chamber on a continual basis and are returned to the donor/patient. In this embodiment, the balloon has taken the shape of the chamber and acts as a leukoreduction system chamber. Once the chamber has collected an appropriate amount of WBCs, the rotor speed is lowered which decreases the fluid pressure in the system. Once the pressure drops below a threshold level the membrane may be able to return to its original shape, either an open or closed ended cylinder. In this state, the WBC's can be collected from the chamber in a highly concentrated fashion.

As noted above, in embodiments, the membrane may be attached to the rigid chamber in a variety of ways including, without limitation: ultrasonic welding with mechanical capture, over-molding, use of barb-lock type fixation device.

ADDITIONAL EMBODIMENTS

Embodiment 1

A separation chamber comprising:
a sidewall defining a chamber volume;
a flexible membrane located in the chamber volume and defining a membrane volume;
an inlet in fluid communication with the membrane volume; and
an outlet in fluid communication with the membrane volume.

Embodiment 2

The separation chamber of Embodiment 1, wherein the flexible membrane comprises a material that allows the flexible membrane to expand when a volume of composite liquid is transferred into the membrane volume.

Embodiment 3

The separation chamber of any of the preceding Embodiments, wherein the flexible membrane comprises a material that allows the flexible membrane to expand and contact an inside surface of the side wall when subjected to a first centrifugal force.

Embodiment 4

The separation chamber of any of the preceding Embodiments, wherein the flexible membrane comprises an outer surface with a teardrop shape.

Embodiment 5

The separation chamber of any of the preceding Embodiments, wherein the flexible membrane comprises an outer surface with a cylindrical shape.

Embodiment 6

The separation chamber of any of the preceding Embodiments, wherein the flexible membrane comprises an outer surface with a conical shape.

Embodiment 7

The separation chamber of any of the preceding Embodiments, wherein an inside surface of the flexible membrane comprises a coating.

Embodiment 8

The separation chamber of any of the preceding Embodiments, wherein the coating is hydrophilic.

Embodiment 9

The separation chamber of any of the preceding Embodiments, wherein the coating is hydrophobic.

Embodiment 10

The separation chamber of any of the preceding claims, wherein the side wall has a conical shape.

Embodiment 11

The separation chamber of any of the preceding Embodiments, wherein the side wall comprises a plurality of vents.

Embodiment 12

The separation chamber of any of the preceding Embodiments, wherein the side wall comprises an interior surface with steps.

Embodiment 13

The separation chamber of any of the preceding Embodiments, wherein the inlet port is at a bottom of the side wall.

Embodiment 14

The separation chamber of any of the preceding Embodiments, further comprising a cap that engages a top of the side wall and further defines the chamber volume.

Embodiment 15

The separation chamber of Embodiment 14, wherein the outlet port is in the cap.

Embodiment 16

The separation chamber of Embodiments 14 or 15, wherein the inlet port is in the cap.

Embodiment 17

The separation chamber of any of the preceding Embodiments, wherein the inlet port is fluidly connected to a blood processing vessel.

Embodiment 18

The separation chamber of any of the preceding Embodiments, further comprising a one-way valve fluidly connected to the inlet port and, wherein the one-way valve allows a flow of composite liquid into the membrane volume.

Embodiment 19

The separation chamber of Embodiment 18, wherein the one-way valve is positioned in the chamber volume.

Embodiment 20

A blood cell collection system comprising:
a centrifuge rotor;
a blood processing vessel mounted on said rotor;
a cell separation chamber in fluid communication with a blood processing vessel;
the cell separation chamber comprising an inlet and an outlet; and
a flexible membrane defining a membrane volume and being positioned in the cell separation chamber, wherein the inlet and the outlet of the cell separation chamber are in fluid communication with the membrane volume.

Embodiment 21

The blood cell collection system of Embodiment 20, wherein the flexible membrane comprises a material that allows the flexible membrane to expand when a volume of liquid comprising cells is transferred into the membrane volume.

Embodiment 22

The blood cell collection system of any of the preceding Embodiments, wherein the flexible membrane comprises a material that allows the flexible membrane to expand and contact an inside surface of the cell separation chamber when subjected to a first centrifugal force.

Embodiment 23

The blood cell collection system of any of the preceding Embodiments, wherein the flexible membrane comprises an outer surface with a teardrop shape.

Embodiment 24

The blood cell collection system of any of the preceding Embodiments, wherein the flexible membrane comprises an outer surface with a cylindrical shape.

Embodiment 25

The blood cell collection system of any of the preceding Embodiments, wherein the flexible membrane comprises an outer surface with a conical shape.

Embodiment 26

The blood cell collection system of any of the preceding Embodiments, wherein an inside surface of the flexible membrane comprises a coating.

Embodiment 27

The blood cell collection system of any of the preceding Embodiments, wherein the coating is hydrophilic.

Embodiment 28

The blood cell collection system of any of the preceding Embodiments, wherein the coating is hydrophobic.

Embodiment 29

The blood cell collection system of any of the preceding Embodiments, wherein the cell separation chamber has a conical shape.

Embodiment 30

The blood cell collection system of any of the preceding Embodiments, wherein the cell separation chamber further comprises a plurality of vents.

Embodiment 31

The blood cell collection system of any of the preceding Embodiments, wherein the cell separation chamber further comprises a plurality of vents.

Embodiment 32

The blood cell collection system of any of the preceding Embodiments, wherein the inlet port is at a bottom of the cell separation chamber.

Embodiment 33

The blood cell collection system of claim of any of the preceding claims, wherein the separation chamber further comprises a cap.

Embodiment 34

The blood cell collection system of Embodiment 33, wherein the outlet is in the cap.

Embodiment 35

The blood cell collection system of Embodiment 33 or Embodiment 34, wherein the inlet is in the cap.

Embodiment 36

The blood cell collection system of any of the preceding Embodiments, wherein the inlet is fluidly connected to a one-way valve that allows a flow of liquid into the membrane volume.

Embodiment 37

A disposable blood separation set comprising:
a blood processing vessel adapted to be mounted on a centrifuge rotor; and
a flexible membrane defining a membrane volume, wherein an inlet and an outlet are in fluid communication with the membrane volume.

Embodiment 38

The disposable blood separation set of Embodiment 37, wherein the flexible membrane comprises a material that allows the flexible membrane to expand when a volume of liquid comprising cells is transferred into the membrane volume.

Embodiment 39

The disposable blood separation set of any of the preceding claims, wherein the flexible membrane comprises a material that allows the flexible membrane to expand when subjected to a first centrifugal force.

Embodiment 40

The disposable blood separation set of any of the preceding Embodiments, wherein the flexible membrane comprises an outer surface with a teardrop shape.

Embodiment 41

The disposable blood separation set of any of the preceding Embodiments, wherein the flexible membrane comprises an outer surface with a cylindrical shape.

Embodiment 42

The disposable blood separation set of any of the preceding Embodiments, wherein the flexible membrane comprises an outer surface with a conical shape.

Embodiment 43

The disposable blood separation set of any of the preceding Embodiments, further comprising a cell separation chamber, wherein the flexible membrane is positioned within the cell separation chamber.

Embodiment 44

The disposable blood separation set of any of the preceding Embodiments, wherein the flexible membrane comprises a material that allows the flexible membrane to expand and contact an inside surface of the cell separation chamber when subjected to a first centrifugal force.

Embodiment 45

A method of separating cellular components, the method comprising:
transferring a liquid comprising whole blood into a blood processing vessel;
separating the liquid comprising whole blood into at least a first component comprising cells and a second component;
transferring the first component into a membrane volume defined by a flexible membrane;
separating cells from the first component in the membrane volume; and
removing the cells from the membrane volume.

Embodiment 46

The method of Embodiment 45, wherein the separating the liquid comprising whole blood comprises, applying a centrifugal force by spinning the blood processing vessel on a rotor.

Embodiment 47

The method of Embodiment 45 or Embodiment 46, wherein the flexible membrane expands during the transferring of the first component into the membrane volume.

Embodiment 48

The method of claim any of the preceding Embodiments, wherein during the removing the cells from the membrane volume, the membrane volume is reduced by contracting of the flexible membrane.

While example embodiments and applications of the present invention have been illustrated and described, it is to be understood that the invention is not limited to the precise configuration, features, designs, steps, or other resources described above. Various modifications, changes, and variations apparent to those skilled in the art may be made in the arrangement, operation, and details of the methods, systems, and devices of the present invention disclosed herein without departing from the scope of the claimed invention.

What is claimed is:

1. A method of separating components of whole blood, the method comprising:
transferring a liquid comprising whole blood into a blood processing vessel adapted to be mounted on a rotor;
separating the liquid comprising whole blood into at least a first component comprising cells and a second component by rotating the blood processing vessel on the rotor;
transferring the first component into a membrane volume defined by a flexible membrane movable from a contracted configuration to an expanded configuration, an inlet into the membrane volume is in fluid communication with an outlet of the blood processing vessel such that the first component flows from the blood processing vessel into the membrane volume for further separation, the flexible membrane is seated in a chamber volume defined by a stepped side wall of a cell separation chamber such that upon transferring the first component into the flexible membrane the flexible membrane expands from the contracted configuration to the expanded configuration, in the expanded configuration the flexible membrane contacts the stepped side wall to give the flexible membrane an expanded, stepped configuration;

separating cells from the first component in the membrane volume by rotating the cell separation chamber; and removing the cells from the membrane volume, thereby allowing the flexible membrane to contract from the expanded, stepped configuration to the contracted configuration.

2. The method of claim 1, wherein during the removing the cells from the membrane volume, the membrane volume is reduced by contracting of the flexible membrane.

3. The method of claim 1 wherein the membrane volume is offset from an axis of rotation of the rotor.

4. The method of claim 3 wherein the first component is transferred into the membrane volume at a first location adjacent the axis of rotation.

5. The method of claim 4 wherein the cells are removed from the membrane volume at a second location adjacent the axis of rotation.

6. The method of claim 4 wherein the cells are transferred into the membrane volume through a tube extending into the membrane volume.

7. The method of claim 3 wherein the membrane volume is located within the separation chamber, said separation chamber defining a predetermined chamber volume, and wherein said membrane volume expands and contracts within said chamber volume.

8. The method of claim 7 wherein the stepped side wall is a frustro-conical side wall.

9. The method of claim 3 wherein the liquid comprising whole blood can flow substantially continuously into the blood processing vessel.

10. The method of claim 1, wherein the flexible membrane has a thickness that tapers along a length of the flexible membrane.

11. The method of claim 1, wherein the first component includes a buffy coat having white blood cells;
 wherein the separating cells from the first component in the membrane volume includes separating white blood cells from the buffy coat; and
 wherein the removing the cells from the membrane volume includes removing the white blood cells from the membrane volume.

* * * * *